(12) United States Patent
List et al.

(10) Patent No.: US 11,287,428 B2
(45) Date of Patent: Mar. 29, 2022

(54) PD1 AND PDL-1 EXPRESSION DURING PROGRESSION FROM MYELODYSPLASTIC SYNDROME TO ACUTE MYELOGENOUS LEUKEMIA

(71) Applicant: H. Lee Moffitt Cancer Center and Research Institute, Inc., Tampa, FL (US)

(72) Inventors: Alan List, Tampa, FL (US); Sheng Wei, Tampa, FL (US)

(73) Assignee: H. Lee Moffitt Cancer Center and Research Institute, Inc., Tampa, FL (US)

( * ) Notice: Subject to any disclaimer, the term of this patent is extended or adjusted under 35 U.S.C. 154(b) by 665 days.

(21) Appl. No.: 16/081,229

(22) PCT Filed: Mar. 16, 2017

(86) PCT No.: PCT/US2017/022767
§ 371 (c)(1),
(2) Date: Aug. 30, 2018

(87) PCT Pub. No.: WO2017/161154
PCT Pub. Date: Sep. 21, 2017

(65) Prior Publication Data
US 2021/0239703 A1    Aug. 5, 2021

Related U.S. Application Data

(60) Provisional application No. 62/309,042, filed on Mar. 16, 2016.

(51) Int. Cl.
| | |
|---|---|
| *G01N 33/574* | (2006.01) |
| *C07K 16/28* | (2006.01) |
| *A61K 39/00* | (2006.01) |
| *A61K 31/00* | (2006.01) |

(52) U.S. Cl.
CPC ... *G01N 33/57426* (2013.01); *C07K 16/2818* (2013.01); *C07K 16/2827* (2013.01); *A61K 31/00* (2013.01); *A61K 39/001129* (2018.08); *G01N 2333/70521* (2013.01); *G01N 2800/7028* (2013.01)

(58) Field of Classification Search
None
See application file for complete search history.

(56) References Cited

U.S. PATENT DOCUMENTS

| 8,217,149 B2 | 7/2012 | Irving et al. |
| 2016/0067336 A1 | 3/2016 | Fandi et al. |

FOREIGN PATENT DOCUMENTS

| JP | 2008051711 A | 3/2008 |
| WO | 2011066389 A1 | 6/2011 |
| WO | 2013023015 A2 | 2/2013 |

OTHER PUBLICATIONS

International Search Report issued for PCT/US2017/022767, dated Jun. 26, 2017.
Yang et al., Expression of PD-L1, PD-L2, PD-1 and CTLA4 in myelodysplastic syndromes is enhanced by treatment with hypomethylating agents, Leukemia vol. 28, 1280-1288, 2014.
Zhang et al., PD-1/PD-L1 interactions inhibit antitumor immune responses in a murine acute myeloid leukemia model, Blood vol. 114, No. 8, 1545-1552, 2009.
Pardoll, The blockade of immune checkpoints in cancer immunotherapy, Nat Rev Cancer 12(4):252-264, 2016.

*Primary Examiner* — Brad Duffy
*Assistant Examiner* — Cheom-Gil Cheong
(74) *Attorney, Agent, or Firm* — Thomas | Horstemeyer, LLP

(57) ABSTRACT

The present disclosure relates to a method for diagnosing in a subject the progression from myelodysplastic syndrome (MDS) to acute myelogenous leukemia (AML). Also disclosed are methods of treating AML in a subject diagnosed by the disclosed methods.

9 Claims, 34 Drawing Sheets

PD1 AND PDL-1 EXPRESSION DURING PROGRESSION FROM MYELODYSPLASTIC SYNDROME TO ACUTE MYELOGENOUS LEUKEMIA

CROSS REFERENCE TO RELATED APPLICATIONS

This application claims the benefit of U.S. Provisional Patent Application Ser. No. 62/309,042 filed Mar. 16, 2016, the disclosure of which is expressly incorporated herein by reference.

FIELD

The present disclosure relates to a method for diagnosing in a subject the progression from myelodysplastic syndrome (MDS) to acute myelogenous leukemia (AML). Also disclosed are methods of treating AML in a subject diagnosed by the disclosed methods.

BACKGROUND

The myelodysplastic syndromes (MDS) are hematological medical conditions with ineffective production of all blood cells. Patients with MDS can develop severe anemia and require blood transfusions. In some cases, the disease worsens and the patient develops cytopenias (low blood counts) caused by progressive bone marrow failure. The outlook in MDS depends on the type and severity. Many people live normal lifespans with MDS. MDS is thought to arise from mutations in the multi-potent bone marrow stem cell, but the specific defects responsible for these diseases remain poorly understood. Differentiation of blood precursor cells is impaired, and there is a significant increase in levels of apoptotic cell death in bone marrow cells. Clonal expansion of the abnormal cells results in the production of cells which have lost the ability to differentiate. If the overall percentage of bone marrow myeloblasts rises over a particular cutoff (20% for WHO and 30% for FAB), then transformation to acute myelogenous leukemia (AML) is said to have occurred. The progression of MDS to AML is a good example of the multi-step theory of carcinogenesis in which a series of mutations occur in an initially normal cell and transform it into a cancer cell.

The goals of MDS therapy are to control symptoms, improve quality of life, improve overall survival, and decrease progression to AML. Once that progression has occurred, AML is treated initially with chemotherapy aimed at inducing a remission; patients may go on to receive additional chemotherapy or a hematopoietic stem cell transplant. What is needed are new diagnostics for diagnosing the progression of MDS to AML.

SUMMARY

As disclosed herein, CD71+ progenitor cells and CD34+ progenitor cells from myelodysplastic syndrome (MDS) patient bone marrow specimens have increased PD-1 expression. Likewise, CD33+ myeloid derived stem cells (MDSCs) from MDS patient BM specimens have increased PD-L1 expression. S100A9 is shown herein to be able to directly induce the expression of PD-1 and PD-L1 in these cells, and to increase apoptosis by activating caspase 3. Also as shown herein, PD-1 and PD-L1 expression shifts during progression from MDS to acute myelogenous leukemia (AML). PD-L1 expression is increased in MDSCs in MDS, but not AML. In contrast, PD-1 expression is dramatically increased in MDS and then continues to rise during progression to AML.

Therefore, disclosed herein is a method for diagnosing in a subject the progression of MDS to AML. The method can involve assaying a sample from the subject for the expression of PD-1 on CD71+ and/or CD34+ progenitor cells, wherein an increase in PD-1 expression on CD71+ and/or CD34+ progenitor cells is an indication of progression from MDS to AML. The method can involve assaying a sample from the subject for the expression of PD-L1 on CD33+ myeloid derived stem cells (MDSCs), wherein a decrease in PD-L1 expression on MDSCs compared to MDS, or a level of PD-L1 expression on MDSCs that is not increased compared to healthy controls, is an indication of progression from MDS to AML.

In one aspect, disclosed herein is a method for diagnosing in a subject the progression of myelodysplastic syndrome (MDS) to acute myelogenous leukemia (AML) comprising assaying a sample from the subject for the expression of PD-1 on CD71+ and CD34+ progenitor cells, the expression of PD-L1 on CD33+ myeloid derived stem cells (MDSCs), or a combination thereof, wherein an increase in PD-1 expression on progenitor cells or decrease in PD-L1 expression on MDSCs is an indication of progression from MDS to AML.

In another aspect, disclosed herein is a method for diagnosing in a subject the progression of myelodysplastic syndrome (MDS) to acute myelogenous leukemia (AML) comprising:

assaying a sample from the subject for the expression of PD-1 on CD71+ and CD34+ progenitor cells, the expression of PD-L1 on CD33+ myeloid derived stem cells (MDSCs), or a combination thereof;

comparing the expression of PD-1 on CD71+ and CD34+ progenitor cells, the expression of PD-L1 on CD33+ myeloid derived stem cells (MDSCs), or a combination thereof, to a healthy control;

wherein an increase in PD-1 expression on progenitor cells or decrease in PD-L1 expression on MDSCs compared to the healthy control is an indication of progression from MDS to AML.

In one embodiment, the method comprises assaying a sample from the subject for the expression of PD-1 on CD71+ and CD34+ progenitor cells, wherein an increase in PD-1 expression on progenitor cells is an indication of progression from MDS to AML. In one embodiment, the method assaying a sample from the subject for the expression of PD-L1 on CD33+ myeloid derived stem cells (MDSCs), wherein a decrease in PD-L1 expression on MDSCs is an indication of progression from MDS to AML. In one embodiment, the method comprises assaying a sample from the subject for the expression of PD-1 on CD71+ and CD34+ progenitor cells and the expression of PD-L1 on CD33+ myeloid derived stem cells (MDSCs), wherein an increase in PD-1 expression on progenitor cells and a decrease in PD-L1 expression on MDSCs is an indication of progression from MDS to AML. In one embodiment, the increase in PD-1 expression on progenitor cells is at least 5 fold relative to a healthy control. In one embodiment, the decrease in PD-L1 expression on MDSCs is at least 450 fold relative to a healthy control. The method can further involve treating the subject for AML if an increase in PD-1 expression on progenitor cells or decrease in PD-L1 expression on MDSCs is detected.

In one embodiment, the method further comprises treating the subject for AML if an increase in PD-1 expression on progenitor cells or decrease in PD-L1 expression on MDSCs is detected. In one embodiment, the treating the subject for AML comprises administration of a chemotherapeutic agent. In one embodiment, the chemotherapeutic agent is selected from cytarabine, daunorubicin, idarubicin, mitoxantrone, vincristine, Cladribine (Leustatin®, 2-CdA), Fludarabine (Fludara®), Topotecan, Etoposide (VP-16), 6-thioguanine (6-TG), Hydroxyurea (Hydrea®), Corticosteroid drugs, such as prednisone or dexamethasone (Decadron®), Methotrexate (MTX), 6-mercaptopurine (6-MP), Azacitidine (Vidaza®), or Decitabine (Dacogen®).

In one embodiment, the treating the subject for AML comprises administration of an immunotherapeutic agent. In one embodiment, the immunotherapeutic agent is selected from an anti-PD1 antibody, an anti-PDL1 antibody, an anti-CTLA4 antibody, or a combination thereof. In one embodiment, the sample is a blood sample.

The details of one or more embodiments of the invention are set forth in the accompanying drawings and the description below. Other features, objects, and advantages of the invention will be apparent from the description and drawings, and from the claims.

DESCRIPTION OF DRAWINGS

The accompanying figures, which are incorporated in and constitute a part of this specification, illustrate several aspects described below.

DETAILED DESCRIPTION

Definitions

Figure 1:
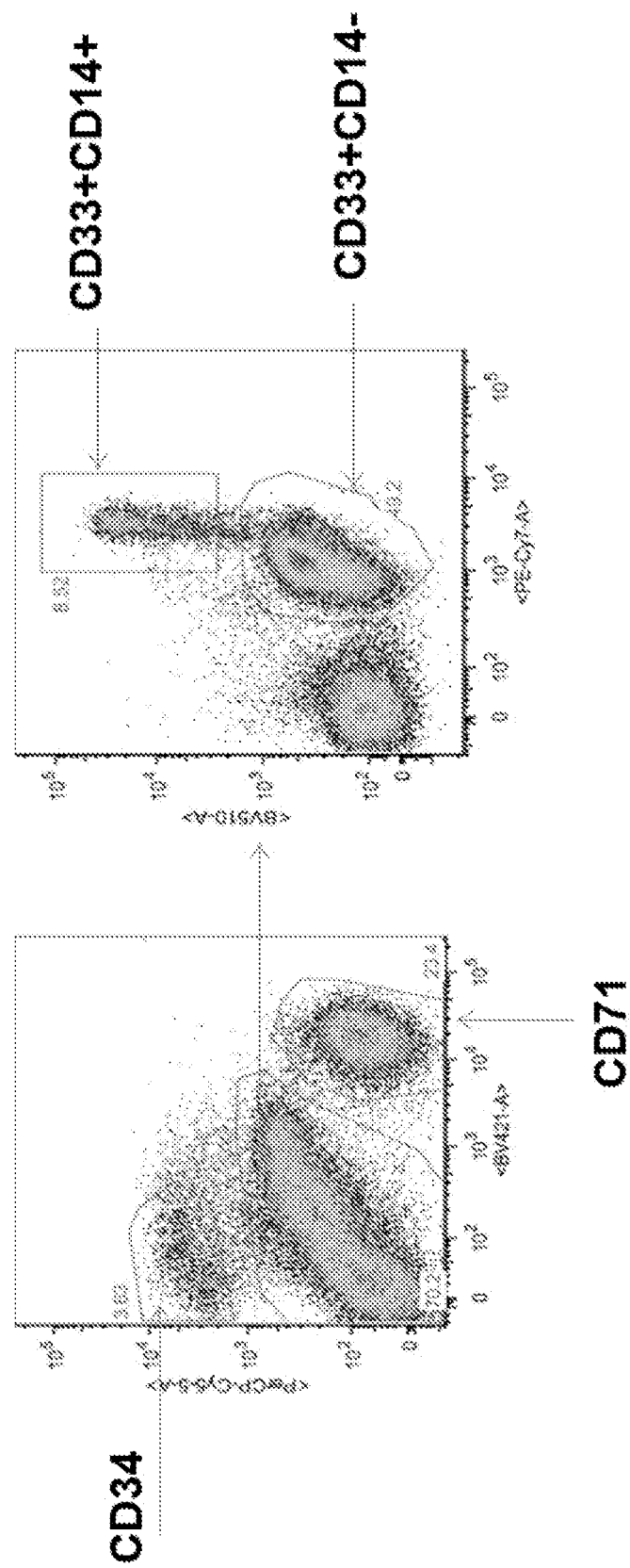
FIG. 1. Gating strategy for expression of PD-1 on CD71+ and CD34+ cells, and PD-L1 on CD33+ cells.

The term "subject" refers to any individual who is the target of a diagnostic assay or administration or treatment. The subject can be a vertebrate, for example, a mammal. Thus, the subject can be a human or veterinary patient. The term "patient" refers to a subject under the treatment of a clinician, e.g., physician.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

As used herein, "increased expression" refers to a 5%, 10%, 20%, 30%, 40%, 50%, 60%, 70%, 80%, 90%, 100%, 200% or higher increase in detectable levels of a biomarker when compared to a control.

As used herein, "decreased expression" refers to a 5%, 10%, 20%, 30%, 40%, 50%, 60%, 70%, 80%, 90%, 100%, 200% or higher decrease in detectable levels of a biomarker when compared to a control.

Methods of Treatment

In one aspect, disclosed herein is a method for diagnosing in a subject the progression of myelodysplastic syndrome (MDS) to acute myelogenous leukemia (AML) comprising assaying a sample from the subject for the expression of PD-1 on CD71+ and CD34+ progenitor cells, the expression of PD-L1 on CD33+ myeloid derived stem cells (MDSCs), or a combination thereof, wherein an increase in PD-1 expression on progenitor cells or decrease in PD-L1 expression on MDSCs is an indication of progression from MDS to AML.

In another aspect, disclosed herein is a method for diagnosing in a subject the progression of myelodysplastic syndrome (MDS) to acute myelogenous leukemia (AML) comprising:

assaying a sample from the subject for the expression of PD-1 on CD71+ and CD34+ progenitor cells, the expression of PD-L1 on CD33+ myeloid derived stem cells (MDSCs), or a combination thereof;

comparing the expression of PD-1 on CD71+ and CD34+ progenitor cells, the expression of PD-L1 on CD33+ myeloid derived stem cells (MDSCs), or a combination thereof, to a healthy control;

wherein an increase in PD-1 expression on progenitor cells or decrease in PD-L1 expression on MDSCs compared to the healthy control is an indication of progression from MDS to AML.

In one embodiment, the method comprises assaying a sample from the subject for the expression of PD-1 on CD71+ and CD34+ progenitor cells, wherein an increase in PD-1 expression on progenitor cells is an indication of progression from MDS to AML. In one embodiment, the method assaying a sample from the subject for the expression of PD-L1 on CD33+ myeloid derived stem cells (MDSCs), wherein a decrease in PD-L1 expression on MDSCs is an indication of progression from MDS to AML. In one embodiment, the method comprises assaying a sample from the subject for the expression of PD-1 on CD71+ and CD34+ progenitor cells and the expression of PD-L1 on CD33+ myeloid derived stem cells (MDSCs), wherein an increase in PD-1 expression on progenitor cells and a decrease in PD-L1 expression on MDSCs is an indication of progression from MDS to AML. In one embodiment, the increase in PD-1 expression on progenitor cells is at least 5 fold relative to a healthy control. In one embodiment, the decrease in PD-L1 expression on MDSCs is at least 450 fold relative to a healthy control. The method can further involve treating the subject for AML if an increase in PD-1 expression on progenitor cells or decrease in PD-L1 expression on MDSCs is detected.

In some embodiments, the expression of PD-1 on CD71+ and CD34+ progenitor cells, the expression of PD-L1 on CD33+ myeloid derived stem cells (MDSCs), or a combination thereof, is compared to a healthy control. In some embodiments, the expression of PD-1 on CD71+ and CD34+ progenitor cells, the expression of PD-L1 on CD33+ myeloid derived stem cells (MDSCs), or a combination thereof, is compared to a control sample. In some embodiments, the expression of PD-1 on CD71+ and CD34+ progenitor cells, the expression of PD-L1 on CD33+ myeloid derived stem cells (MDSCs), or a combination thereof, is compared to a control population. In some embodiments, the expression of PD-1 on CD71+ and CD34+ progenitor cells, the expression of PD-L1 on CD33+ myeloid derived stem cells (MDSCs), or a combination thereof, is compared to a non-affected control sample.

In one embodiment, the increase in PD-1 expression on progenitor cells is at least 2 fold (for example, at least 2 fold, at least 3 fold, at least 4 fold, at least 5 fold, at least 10 fold), relative to a healthy control.

In one embodiment, the decrease in PD-L1 expression on MDSCs is at least 2 fold (for example, at least 2 fold, at least 5 fold, at least 10 fold, at least 25 fold, at least 50 fold, at least 100 fold, at least 150 fold, at least 200 fold, at least 250 fold, at least 300 fold, at least 350 fold, at least 400 fold, at least 450 fold, at least 500 fold), relative to a healthy control.

In one embodiment, the method further comprises treating the subject for AML if an increase in PD-1 expression on progenitor cells or decrease in PD-L1 expression on MDSCs is detected. In one embodiment, the treating the subject for AML comprises administration of a chemotherapeutic agent. In one embodiment, the chemotherapeutic agent is selected from cytarabine, daunorubicin, idarubicin, mitoxantrone, vincristine, Cladribine (Leustatin®, 2-CdA), Fludarabine (Fludara®), Topotecan, Etoposide (VP-16), 6-thioguanine (6-TG), Hydroxyurea (Hydrea®), Corticosteroid drugs, such as prednisone or dexamethasone (Decadron®), Methotrexate (MTX), 6-mercaptopurine (6-MP), Azacitidine (Vidaza®), or Decitabine (Dacogen®).

In one embodiment, the treating the subject for AML comprises administration of an immunotherapeutic agent. In one embodiment, the immunotherapeutic agent is selected from an anti-PD1 antibody, an anti-PDL1 antibody, an anti-CTLA4 antibody, or a combination thereof. In one embodiment, the sample is a blood sample.

PD-1 and PD-L1 Expression

In some embodiments, the disclosed method involves assaying a sample from the subject for the expression of PD-1 on CD71+ and/or CD34+ progenitor cells. In some embodiments, the disclosed method involves assaying a sample from the subject for the expression of PD-L1 on CD33+ myeloid derived stem cells (MDSCs).

Therefore, the cluster of differentiation (CD) molecules CD33, CD34, and CD71, are particularly of interest as cell markers of specific cell types. The CD nomenclature was proposed and established in the 1$^{st}$ International Workshop and Conference on Human Leukocyte Differentiation Antigens (HLDA), which was held in Paris in 1982. This system was intended for the classification of the many monoclonal antibodies (mAbs) generated by different laboratories around the world against epitopes on the surface molecules of leukocytes. Since then, its use has expanded to many other cell types, and more than 320 CD unique clusters and subclusters have been identified. While using one CD molecule to define populations is uncommon (though a few examples exist), combining markers has allowed for cell types with very specific definitions within the immune system. Cell populations are usually defined using a '+' or a '−' symbol to indicate whether a certain cell fraction expresses or lacks a CD molecule. For example, a "CD34+, CD31−" cell is one that expresses CD34, but not CD31. This CD combination typically corresponds to a stem cell, opposed to a fully-differentiated endothelial cell.

Therefore, the expression of PD-1 or PD-L1 on the surface of progenitor cells or MDSCs can be determined using flow cytometry immunodetection, e.g., by fluorescence-activated cell sorting (FACS). Suitable antibodies that specifically bind PD-1, PD-L1, CD33, CD34, and CD71 are commercially available.

Clinical samples for use in the disclosed methods may be obtained from a variety of sources, including peripheral blood, bone marrow, lymph, cerebrospinal fluid, and synovial fluid. Such samples can be separated by centrifugation, elutriation, density gradient separation, apheresis, affinity selection, panning, FACS, centrifugation with Hypaque, etc. prior to analysis, and a mononuclear fraction (PBMC) can be used. Once a sample is obtained, it can be used directly, frozen, or maintained in appropriate culture medium for short periods of time. Various media can be employed to maintain cells. The samples may be obtained by any convenient procedure, such as the drawing of blood, venipuncture, biopsy, or the like. Usually a sample will comprise at least about $10^2$ cells, more usually at least about $10^3$ cells, and preferable $10^4$, $10^5$ or more cells. Typically the samples will be from human patients, although animal models may find use, e.g. equine, bovine, porcine, canine, feline, rodent, e.g. mice, rats, hamster, primate, etc.

An appropriate solution may be used for dispersion or suspension of the cell sample. Such solution will generally be a balanced salt solution, e.g. normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc.

Analysis of the cells can use conventional methods. Techniques providing accurate enumeration include fluorescence activated cell sorters, which can have varying degrees of sophistication, such as multiple color channels, low angle and obtuse light scattering detecting channels, impedance channels, etc. The cells may be selected against dead cells by employing dyes associated with dead cells (e.g. propidium iodide).

The affinity reagents may be specific receptors or ligands for the cell surface molecules indicated above. In addition to antibody reagents, peptide-MHC antigen and T cell receptor pairs may be used; peptide ligands and receptors; effector and receptor molecules, and the like. Antibodies and T cell receptors may be monoclonal or polyclonal, and may be produced by transgenic animals, immunized animals, immortalized human or animal B-cells, cells transfected with DNA vectors encoding the antibody or T cell receptor, etc. The details of the preparation of antibodies and their suitability for use as specific binding members are well-known to those skilled in the art.

Of particular interest is the use of antibodies as affinity reagents. Conveniently, these antibodies can be conjugated with a label for use in separation. Labels include magnetic beads, which allow for direct separation, biotin, which can be removed with avidin or streptavidin bound to a support, fluorochromes, which can be used with a fluorescence activated cell sorter, or the like, to allow for ease of separation of the particular cell type. Frequently each antibody is labeled with a different fluorochrome that excite and/or emit with different wavelengths, to permit independent sorting for each marker.

The antibodies are added to a suspension of cells, and incubated for a period of time sufficient to bind the available cell surface antigens. The incubation will usually be at least about 5 minutes and usually less than about 30 minutes. It is desirable to have a sufficient concentration of antibodies in the reaction mixture, such that the efficiency of the separation is not limited by lack of antibody. The appropriate concentration is determined by titration. The medium in which the cells are separated will be any medium that maintains the viability of the cells. A preferred medium is phosphate buffered saline containing from 0.1 to 0.5% BSA. Various media are commercially available and may be used according to the nature of the cells, including Dulbecco's Modified Eagle Medium (dMEM), Hank's Basic Salt Solution (HBSS), Dulbecco's phosphate buffered saline (dPBS), RPMI, Iscove's medium, PBS with 5 mM EDTA, etc., frequently supplemented with fetal calf serum, BSA, HSA, etc. The labeled cells are then quantitated as to the expression of cell surface markers.

Acute Myeloid Leukemia

The disclosed methods can be used to diagnose the progression of a subject from MDS to AML. Therefore, also disclosed is a method of treating a subject that is determined to be progressing towards AML.

In AML, malignant transformation and uncontrolled proliferation of an abnormally differentiated, long-lived myeloid progenitor cell results in high circulating numbers of immature blood forms and replacement of normal marrow by malignant cells. Symptoms include fatigue, pallor, easy bruising and bleeding, fever, and infection; symptoms of leukemic infiltration are present in only about 5% of patients (often as skin manifestations). Treatment includes induction chemotherapy to achieve remission and post-remission chemotherapy (with or without stem cell transplantation) to avoid relapse.

AML has a number of subtypes that are distinguished from each other by morphology, immunophenotype, and cytochemistry. Five classes are described, based on predominant cell type, including myeloid, myeloid-monocytic, monocytic, erythroid, and megakaryocytic. Acute promyelocytic leukemia is a particularly important subtype, representing 10 to 15% of all cases of AML, striking a younger age group (median age 31 yr) and particular ethnicity (Hispanics), in which the patient commonly presents with a coagulation disorder.

Prognostic factors help determine treatment protocol and intensity; patients with strongly negative prognostic features are usually given more intense forms of therapy, because the potential benefits are thought to justify the increased treatment toxicity. The most important prognostic factor is the leukemia cell karyotype; favorable karyotypes include t(15; 17), t(8;21), and inv16 (p13;q22). Negative factors include increasing age, a preceding myelodysplastic phase, secondary leukemia, high WBC count, and absence of Auer rods. The FAB or WHO classification alone does not predict response.

Initial therapy attempts to induce remission. The basic induction regimen includes cytarabine by continuous IV infusion or high doses for 5 to 7 days; daunorubicin or idarubicin is given IV for 3 days during this time. Some regimens include 6-thioguanine, etoposide, vincristine, and prednisone, but their contribution is unclear. Treatment usually results in significant myelosuppression, with infection or bleeding; there is significant latency before marrow recovery. During this time, meticulous preventive and supportive care is vital.

The information thus derived is useful in prognosis and diagnosis, including susceptibility to acceleration of disease, status of a diseased state and response to changes in the environment, such as the passage of time, treatment with drugs or other modalities. The cells can also be classified as to their ability to respond to therapeutic agents and treatments, isolated for research purposes, screened for gene expression, and the like. The clinical samples can be further characterized by genetic analysis, proteomics, cell surface staining, or other means, in order to determine the presence of markers that are useful in classification. For example, genetic abnormalities can be causative of disease susceptibility or drug responsiveness, or can be linked to such phenotypes.

In one embodiment, the treating the subject for AML comprises administration of a therapeutic agent. In one embodiment, the therapeutic agent is an anti-CD33 antibody or an antibody-drug conjugate. In one embodiment, the therapeutic agent is an anti-CD33 antibody. In one embodiment, the therapeutic agent is an antibody-drug conjugate. In some embodiments, the therapeutic agent can be administered in combination with a chemotherapeutic agent or an immunotherapeutic agent.

Immunotherapeutic Agents (Immune Checkpoint Inhibitors)

There are a number of immunotherapeutic agents that are known to inhibit immune checkpoint proteins (immune checkpoint inhibitors). Known immune checkpoint proteins include CTLA-4, PD1 and its ligands PD-L1 and PD-L2 and in addition LAG-3, BTLA, B7H3, B7H4, TIM3, KIR. The pathways involving LAGS, BTLA, B7H3, B7H4, TIM3, and KIR are recognized in the art to constitute immune checkpoint pathways similar to the CTLA-4 and PD-1 dependent pathways (see e.g. Pardoll, 2012. Nature Rev Cancer 12:252-264).

An immune checkpoint inhibitor is any compound inhibiting the function of an immune checkpoint protein. Inhibition includes reduction of function and/or full blockade. In one embodiment, the immune checkpoint protein is a human immune checkpoint protein. Thus, the immune checkpoint protein inhibitor can be an inhibitor of a human immune checkpoint protein Immune checkpoint proteins are described in the art (see for example, Pardoll, 2012. Nature Rev. Cancer 12: 252-264).

Preferred immune checkpoint protein inhibitors are antibodies that specifically recognize immune checkpoint proteins. A number of PD1, PDL-1, PD-L2, CTLA-4, LAG-3, BTLA, B7H3, B7H4, 4-1BB (CD137), TIM3 and KIR inhibitors are known and in analogy of these known immune checkpoint protein inhibitors, alternative immune checkpoint inhibitors may be administered using the devices and methods disclosed herein.

Examples of PD-1 inhibitors include without limitation humanized antibodies blocking human PD-1 such as pembrolizumab (formerly lambrolizumab), or pidilizumab as well as fully human antibodies such as nivolumab (previously known as MDX-1106 or BMS-936558). Ipilimumab is a fully human CTLA-4 blocking antibody presently marketed under the name Yervoy (Bristol-Myers Squibb). A second CTLA-4 inhibitor is tremelimumab. In one embodiment, the immunotherapeutic is nivolumab.

In addition, immune checkpoint inhibitors may include without limitation humanized or fully human antibodies blocking PD-L1 such as MEDI-4736 (disclosed in WO2011066389 A1), MPDL328 OA (disclosed in U.S. Pat. No. 8,217,149 B2) and MIH1 (Affymetrix obtainable via eBioscience (16.5983.82)) and other PD-L1 inhibitors presently under investigation. Additional antibodies to PD-LI include atezolizumab and durvalumab.

In one embodiment, KIR inhibitors are administered. Lirilumab is a human monoclonal antibody that binds to KIR2DL1/2L3. In one embodiment, inhibitors of 4-1BB (CD137) are administered. Urelumab targets the extracellular domain of CD137.

In one embodiment, an immune checkpoint inhibitor is preferably selected from a CTLA-4, PD-1 or PD-L1 inhibitor, such as selected from the known CTLA-4, PD-1 or PD-L1 inhibitors mentioned above (ipilimumab, tremelimumab, pembrolizumab, nivolumab, pidilizumab, atezolizumab, durvalumab, AMP-244, MEDI-4736, MPDL328 OA, MIH1), or combinations thereof.

A number of embodiments of the invention have been described. Nevertheless, it will be understood that various modifications may be made without departing from the spirit and scope of the invention. Accordingly, other embodiments are within the scope of the following claims.

EXAMPLES

The following examples are set forth below to illustrate the compositions, devices, methods, and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Example 1: S100A9 Induction of PD1/PDL-1 in Myelodysplastic Syndrome (MDS)

Experiments were conducted to determine whether PD-1 expressed on progenitors engage with PD-L1 expressed by CD33+ cells to trigger cell death.

Expression of PD-1 on CD71+ and CD34+ Cells, and PD-L1 on CD33+ Cells from MDS Primary Specimens.

Figure 2:
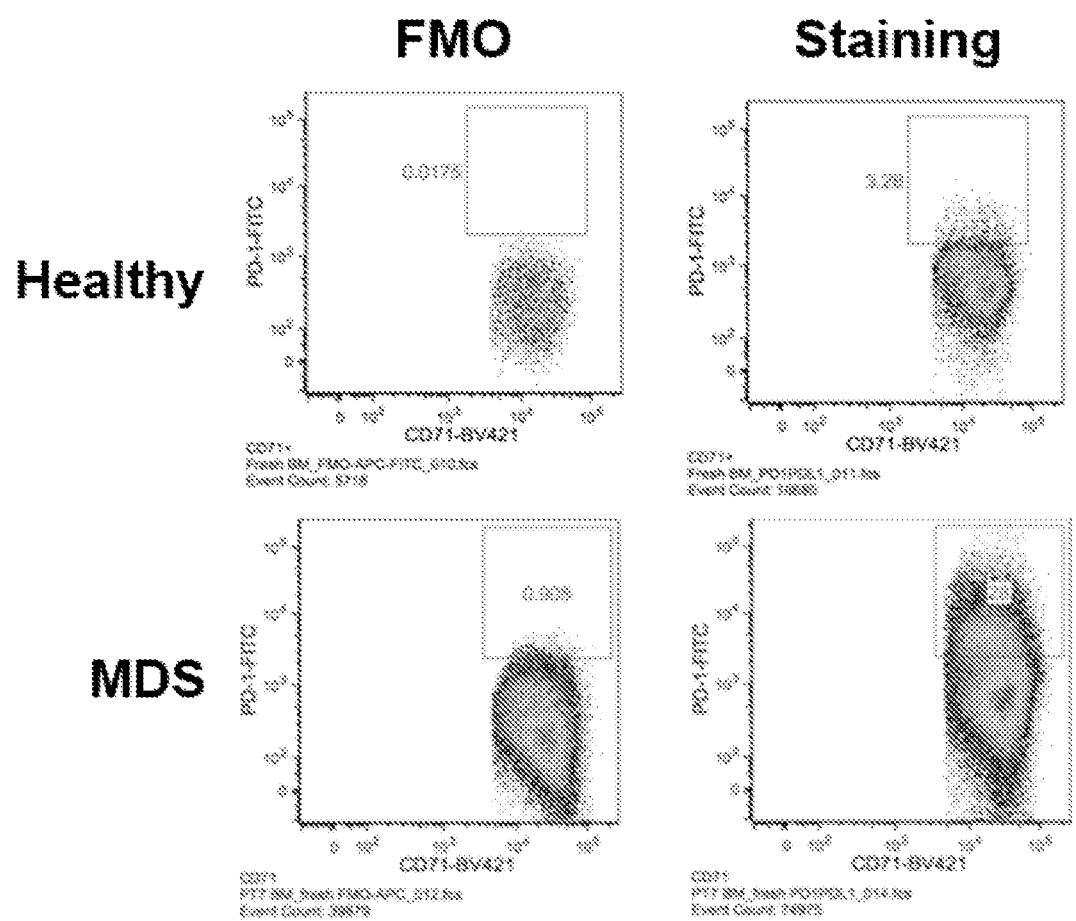
FIG. 2. CD71+ from MDS BM patient specimens have increased PD1 expression.
Figure 3A:
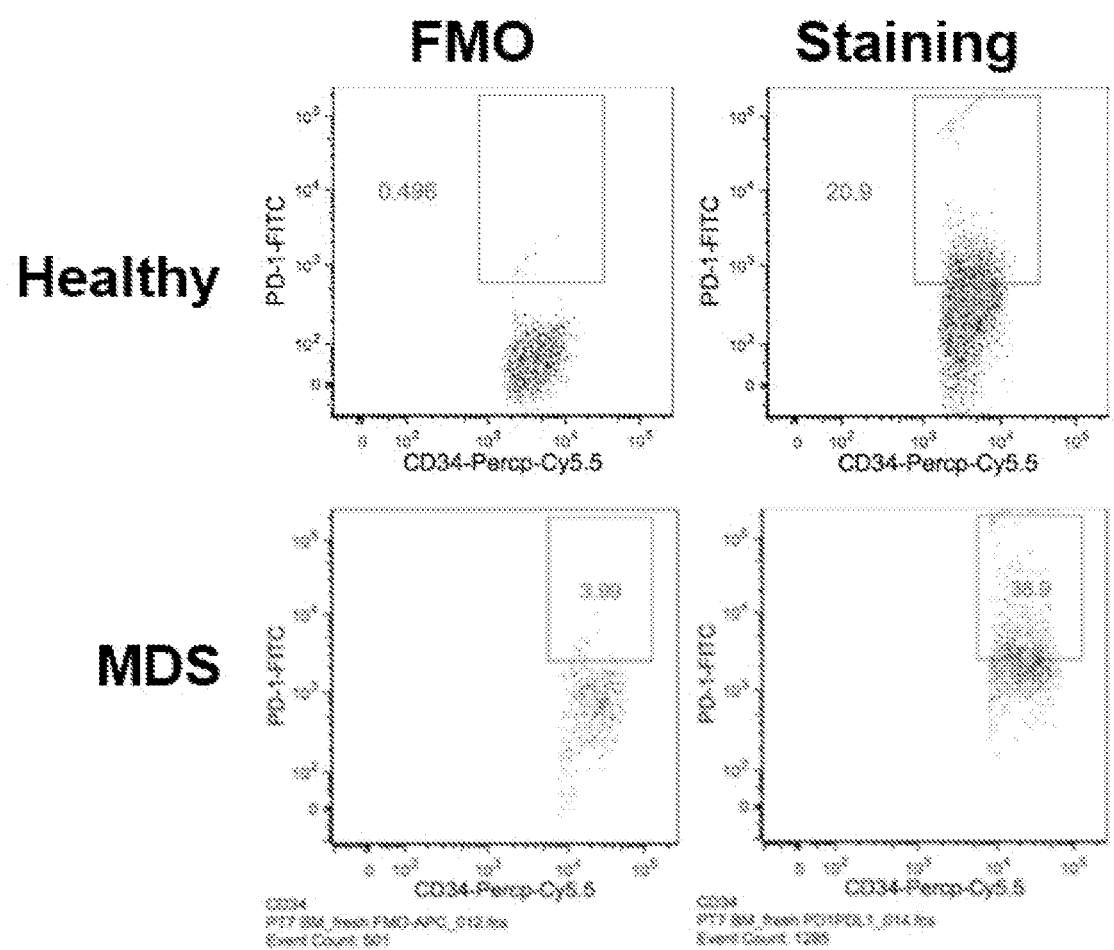
FIGS. 3A and 3B. CD34+ from MDS BM patient specimens have increased PD1 expression.
Figure 3B:
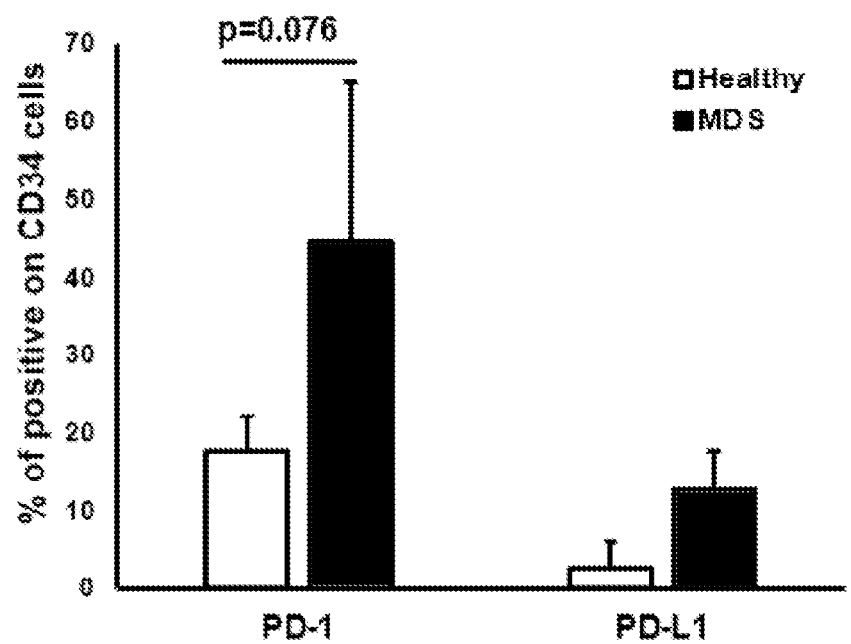
Figure 4A:
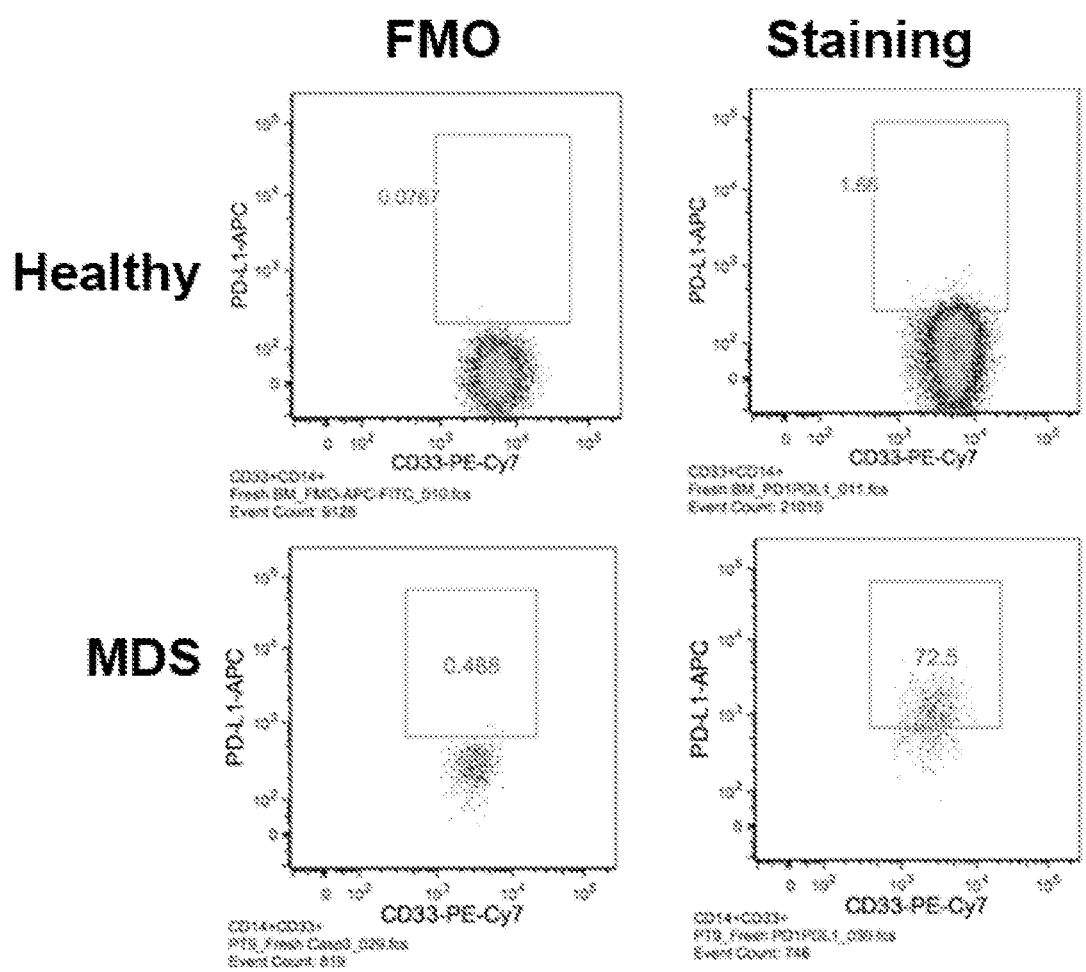
FIGS. 4A to 4C. CD33+CD14+ from MDS BM patient specimens have increased PDL1 expression.
Figure 4B:
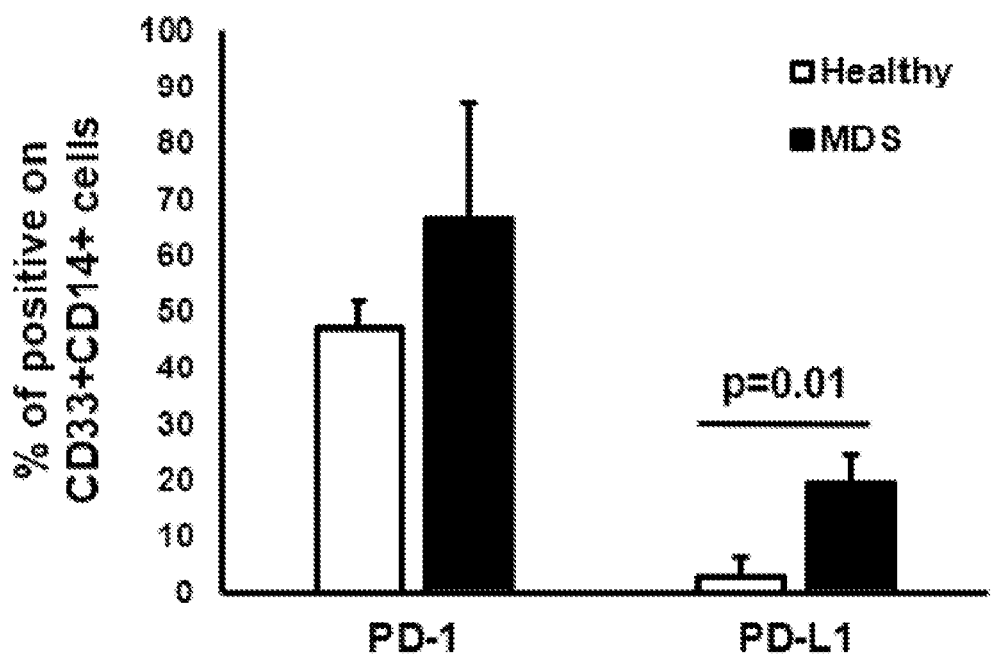
Figure 4C:
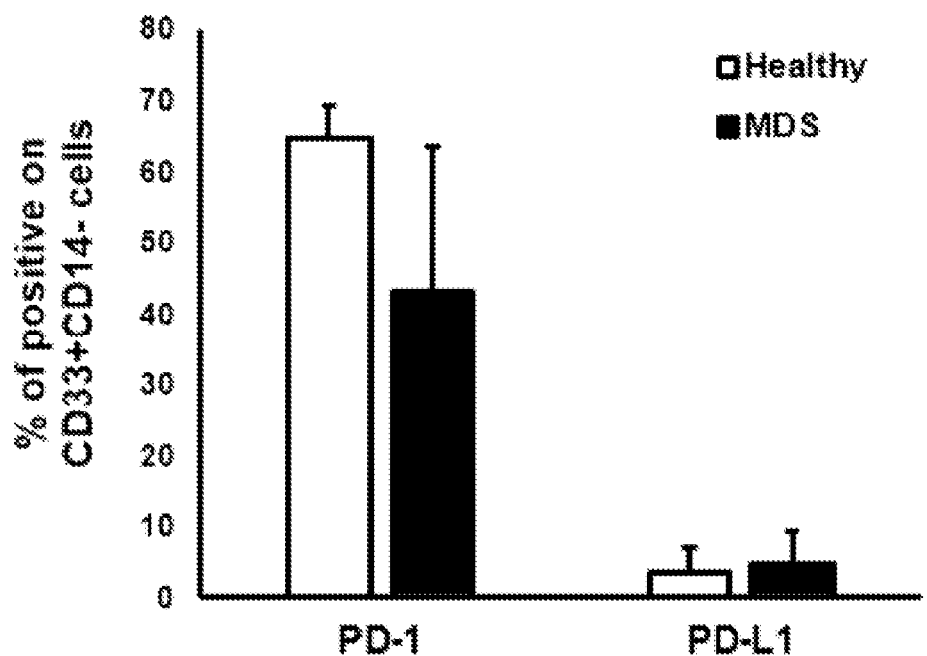

FIG. 1 shows gated strategy for differentiating the expression of PD1 and PDL1 in different blood subsets. As shown in FIGS. 2 and 3A-3B, PD1 expression is increased in CD71 erythroid progenitor cells and CD34 hematopoietic stem cells in MDS compared to healthy donors. Likewise, as shown in FIGS. 4A to 4C, PDL1 expression (the ligand for PD1) is increased in CD33+CD14+ cells in MDS compared to healthy donors.

S100A9 can Directly Induce the Expression of PD-L1 on CD33+ Cells.

Figure 5:
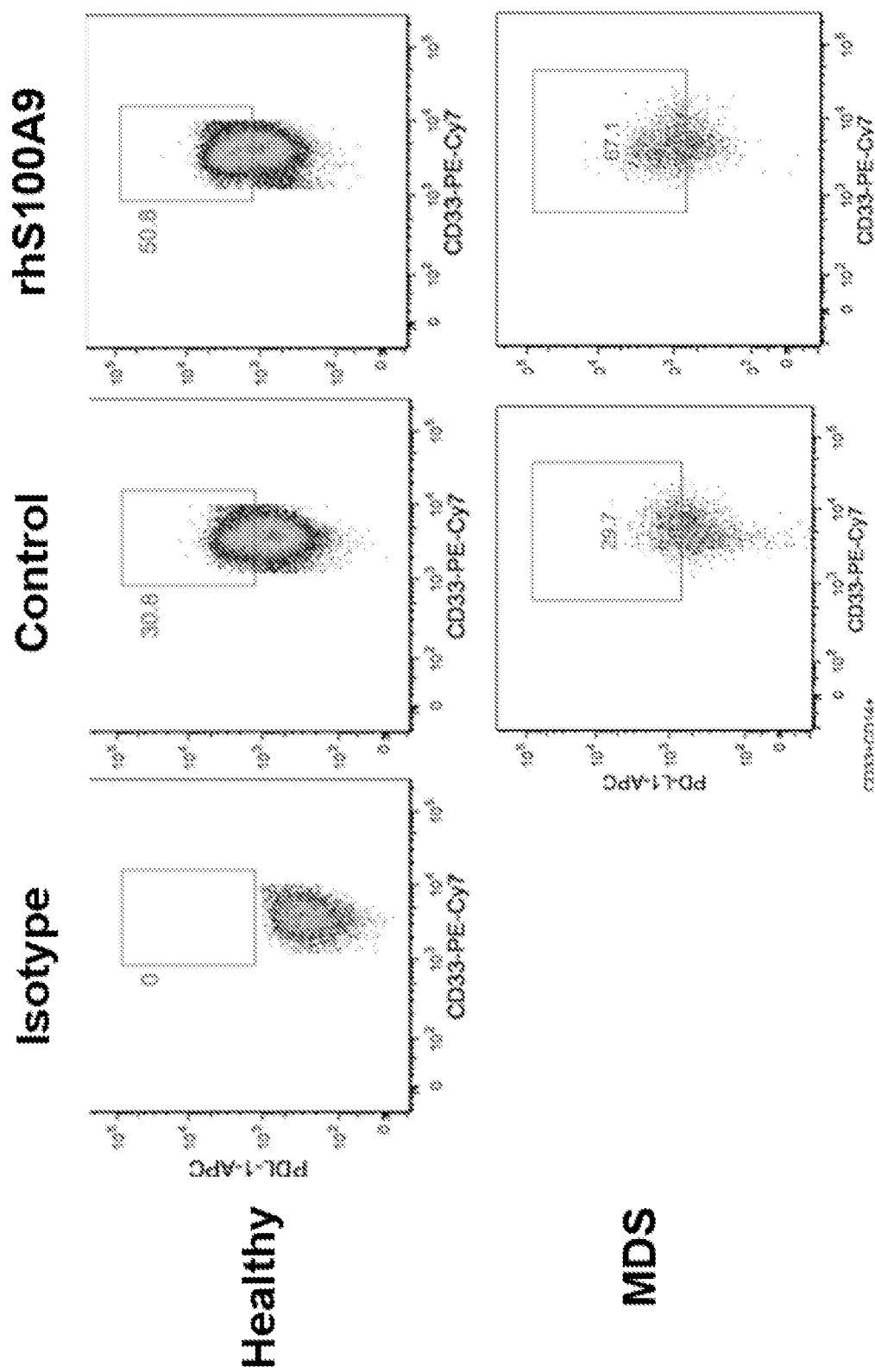
FIG. 5. Culture of BM cells with rhS100A9 can induce the expression of PDL1 on CD33+CD14+.
Figure 6A:
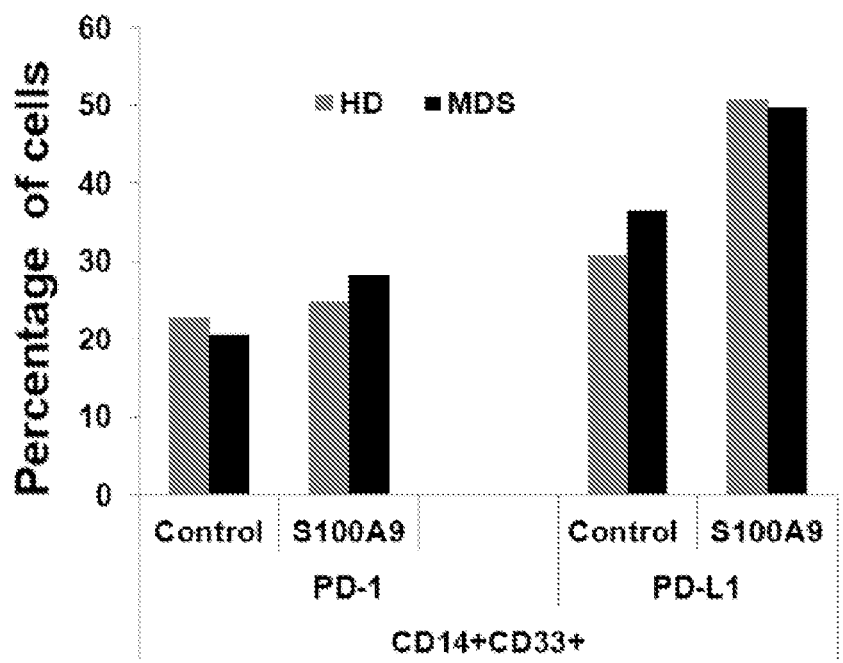
FIGS. 6A and 6B. Culture of BM cells with rhS100A9 can induce the expression of PD1 on CD33+.
Figure 6B:
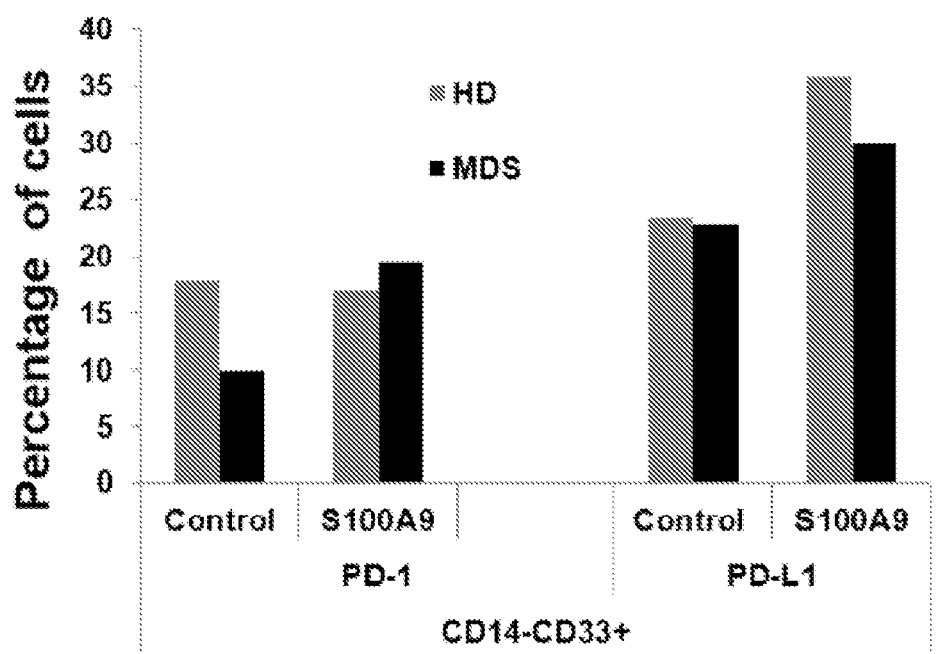
Figure 7:
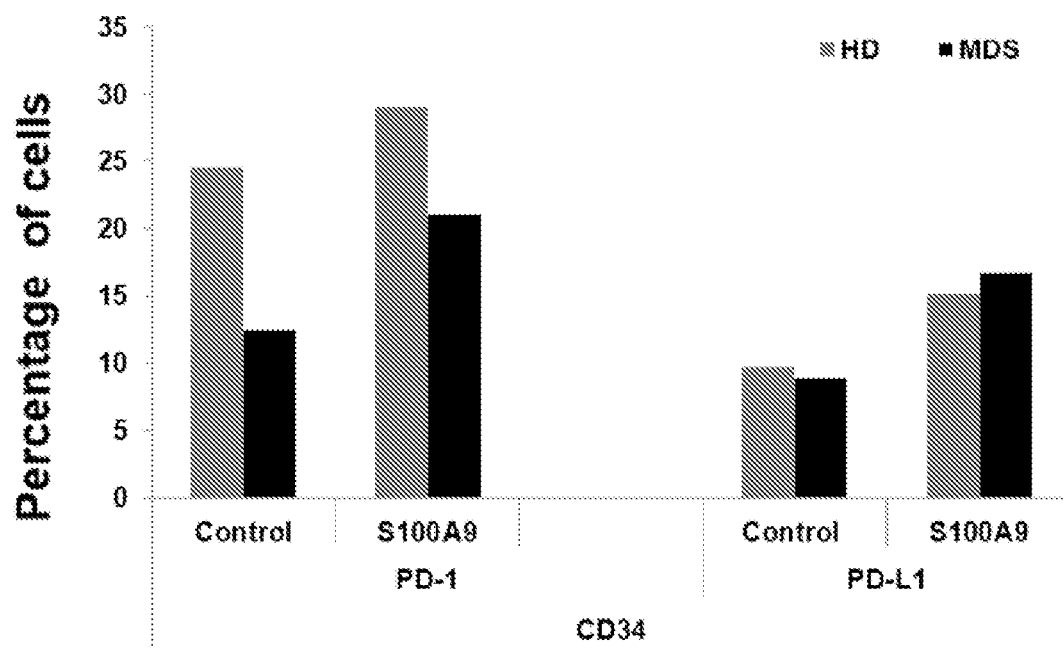
FIG. 7. Culture of BM cells with rhS100A9 can induce the expression of PD1 on CD34+.
Figure 8:
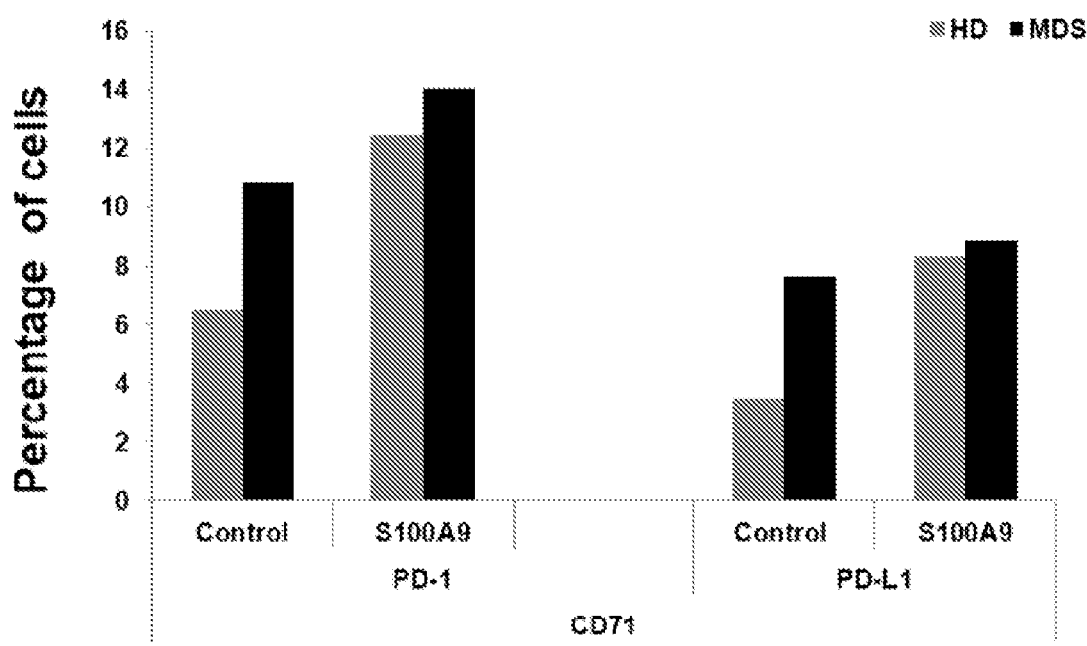
FIG. 8. Culture of BM cells with rhS100A9 can induce the expression of PD1 on CD71+.
Figure 9A:
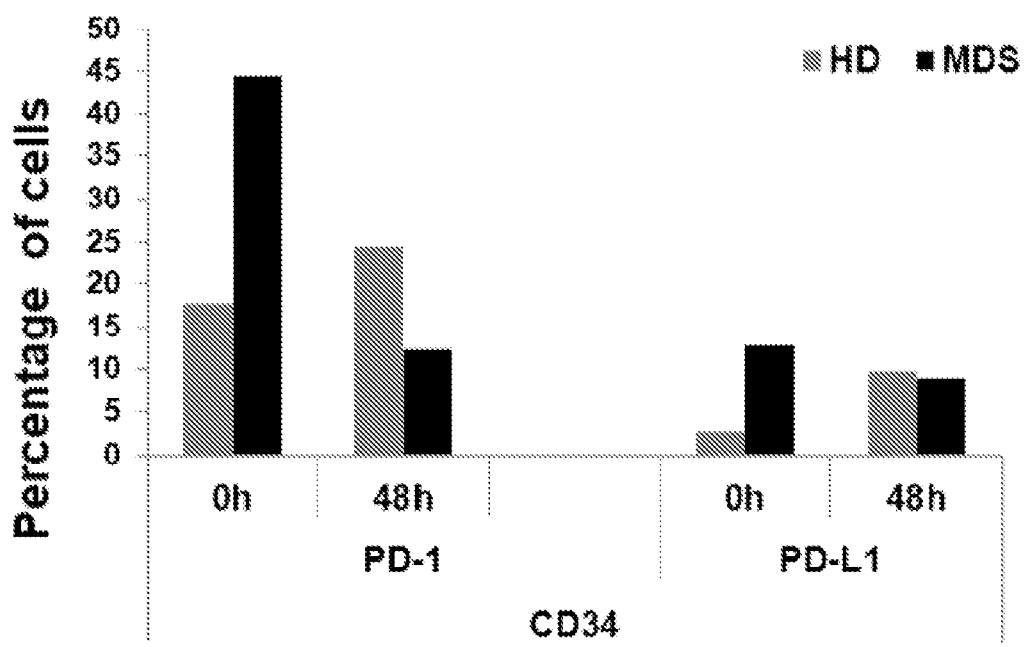
FIGS. 9A and 9B. Culture of BM cells reduces expression of PD1 and PDL1 on CD34+CD71+.
Figure 9B:
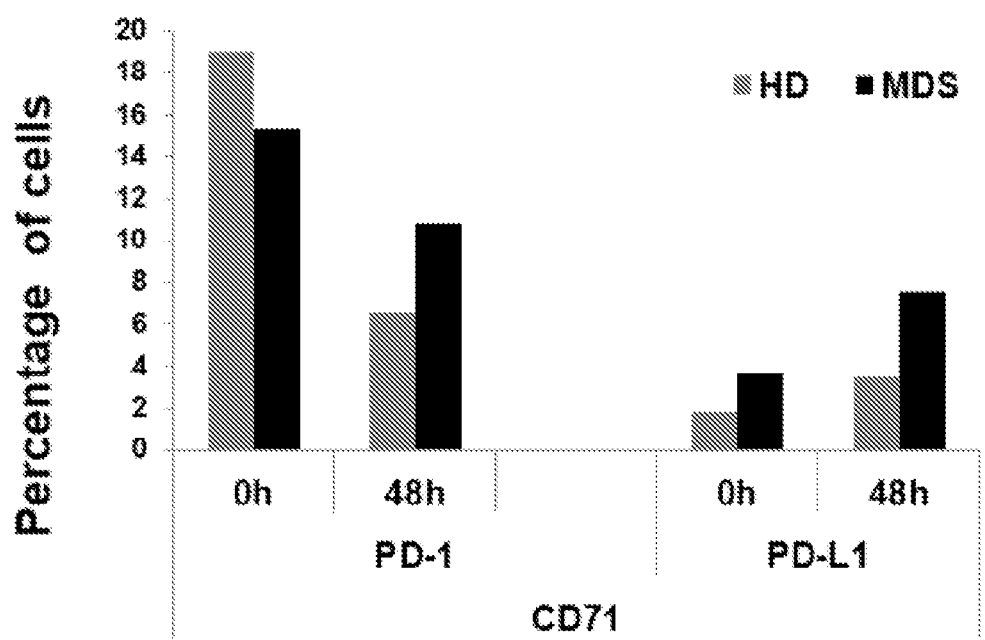

As shown in FIG. 5, treatment with recombinant human S100A9 induces PDL1 expression in CD33+CD14+ cells. Likewise, as shown in FIGS. 6A, 6B, 7, and 8, treatment with recombinant human S100A9 induces PD1 on CD33+, CD34+, and CD71+ cells. In addition, the culture of BM cells reduces expression of PD1 and PDL1 on CD34+ CD71+ (FIGS. 9A and 9B) due to lack of S100A9 stimulation.

Apoptosis by PD-1/PD-L1.

Figure 10:
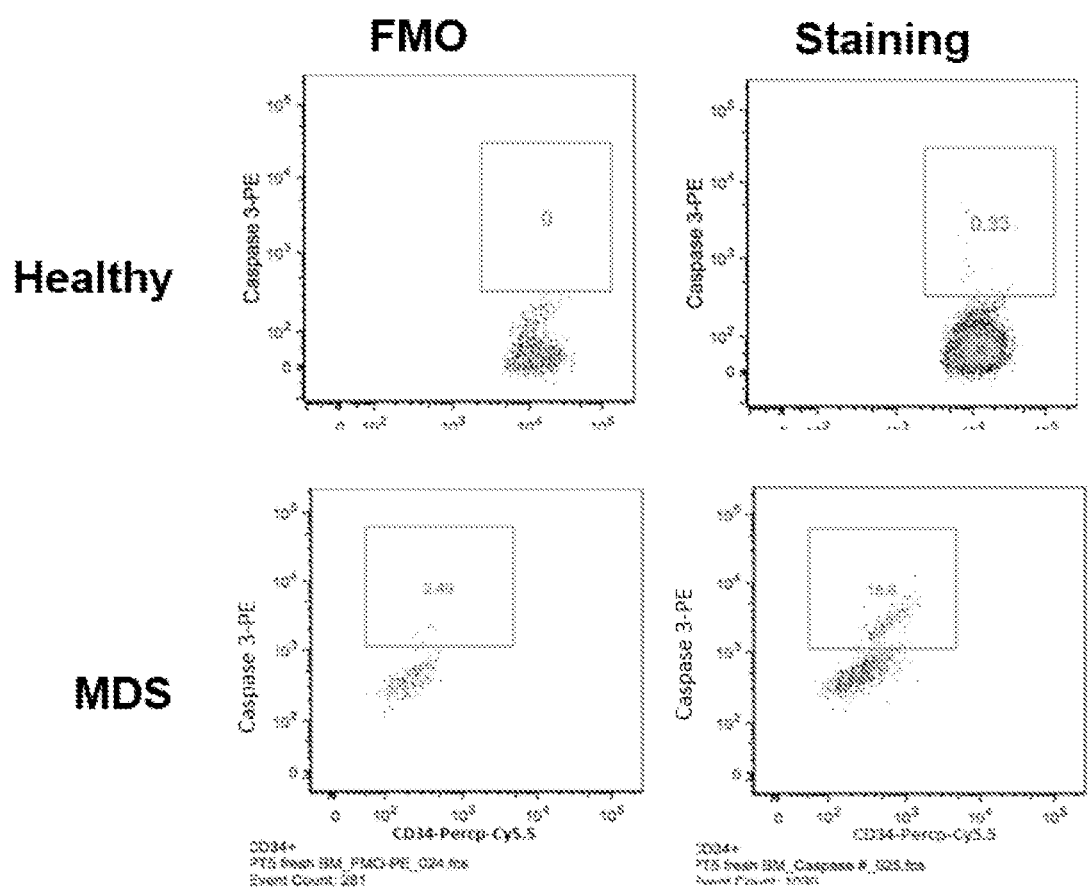
FIG. 10. MDS BMMNCs have increased active caspase3 in CD34 cells compared to healthy BM.
Figure 11:
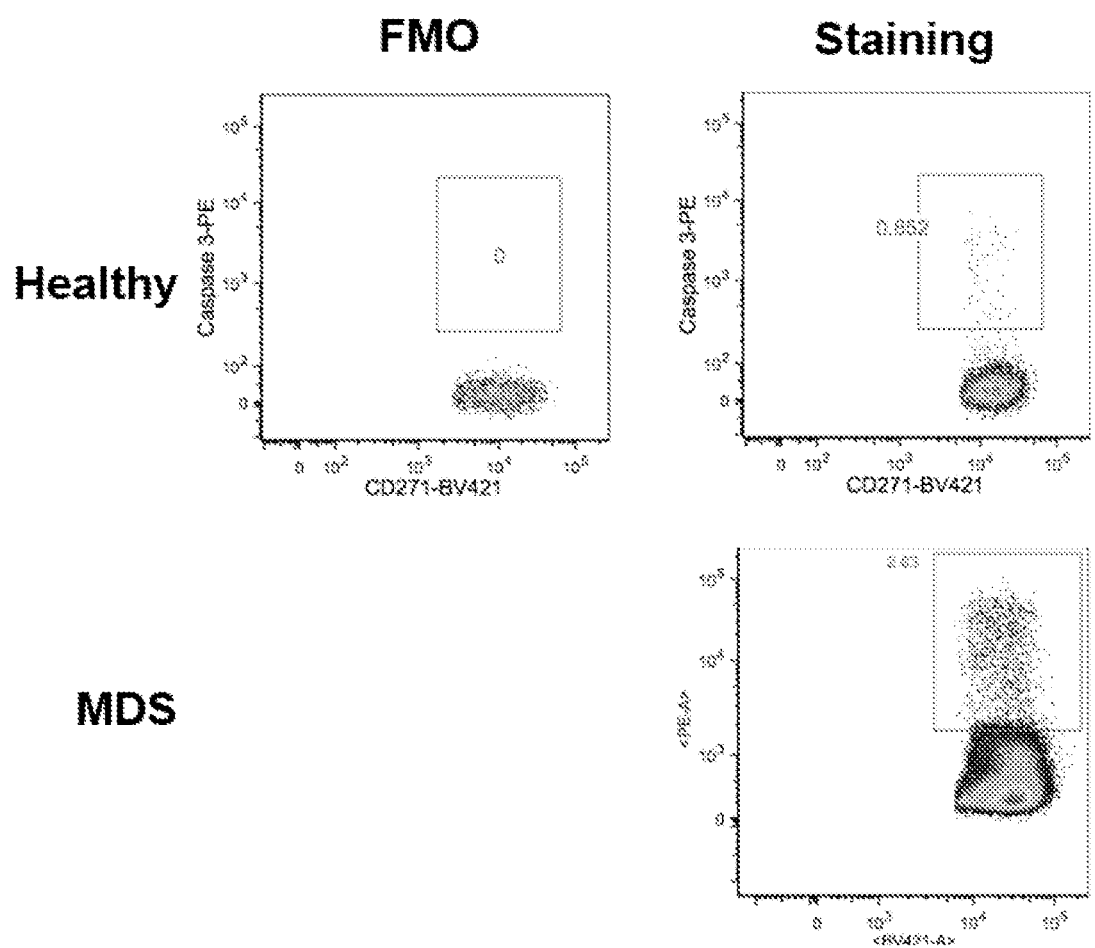
FIG. 11. MDS BMMNCs have increased active caspase3 in CD71 cells compared to healthy BM.
Figure 12A:
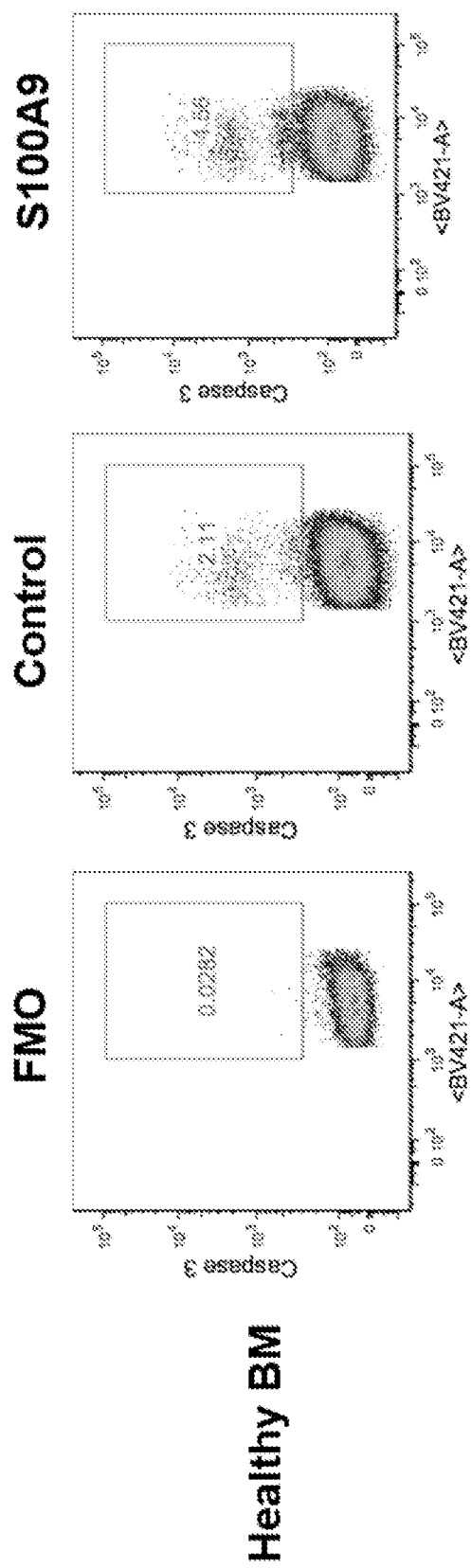
FIGS. 12A and 12B. S100A9 can increase active caspase 3 in CD71 cells.
Figure 12B:
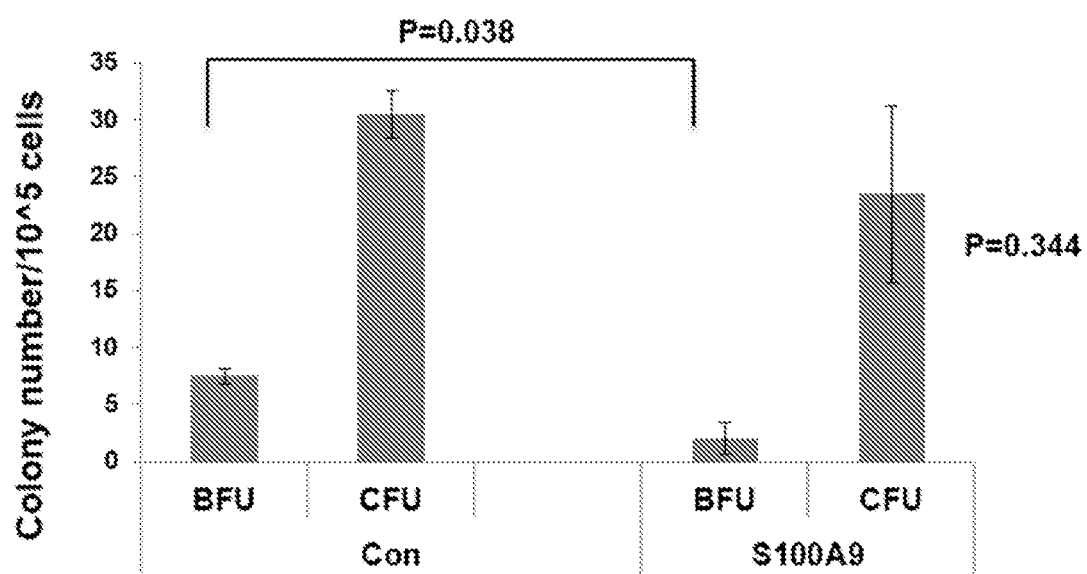
Figure 13:
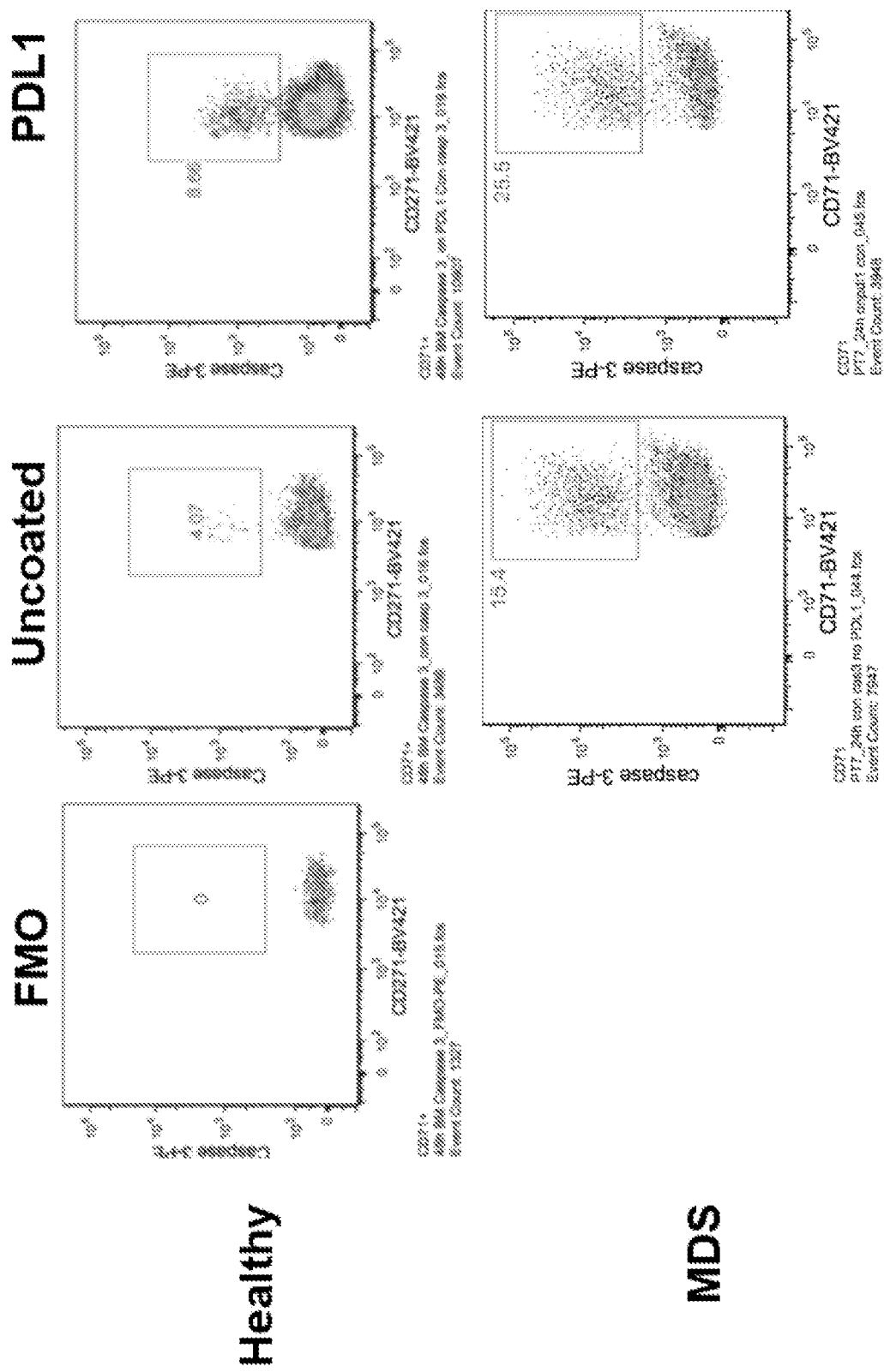
FIG. 13. rhPDL1 can also increase apoptosis of CD71 from BM MNC. BM cells were placed in rhPDL1 coated wells of 24-well plate for 24 h.

As shown in FIGS. 10 and 11, MDS BMMNCs have increased active caspase 3 in CD34 cells and CD71 cells compared to healthy BM. In addition, S100A9 can increase active caspase 3 in CD71 cells (FIGS. 12A and 12B). rhPDL1 can also increase apoptosis of CD71 from BM MNC (FIG. 13).

Figure 14:
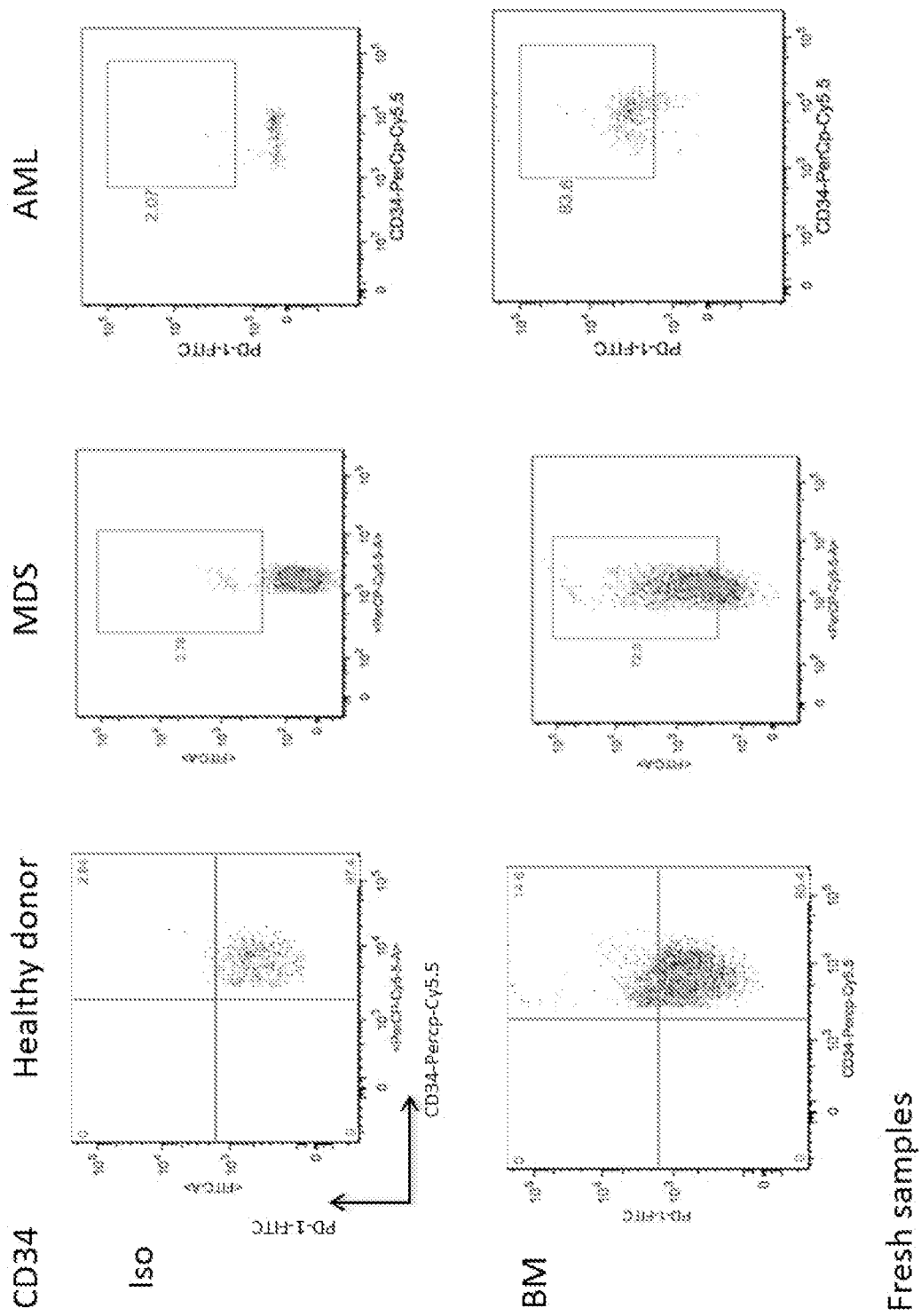
FIG. 14. PD1 expression shifts in stem cells during disease progression.
Figure 15:
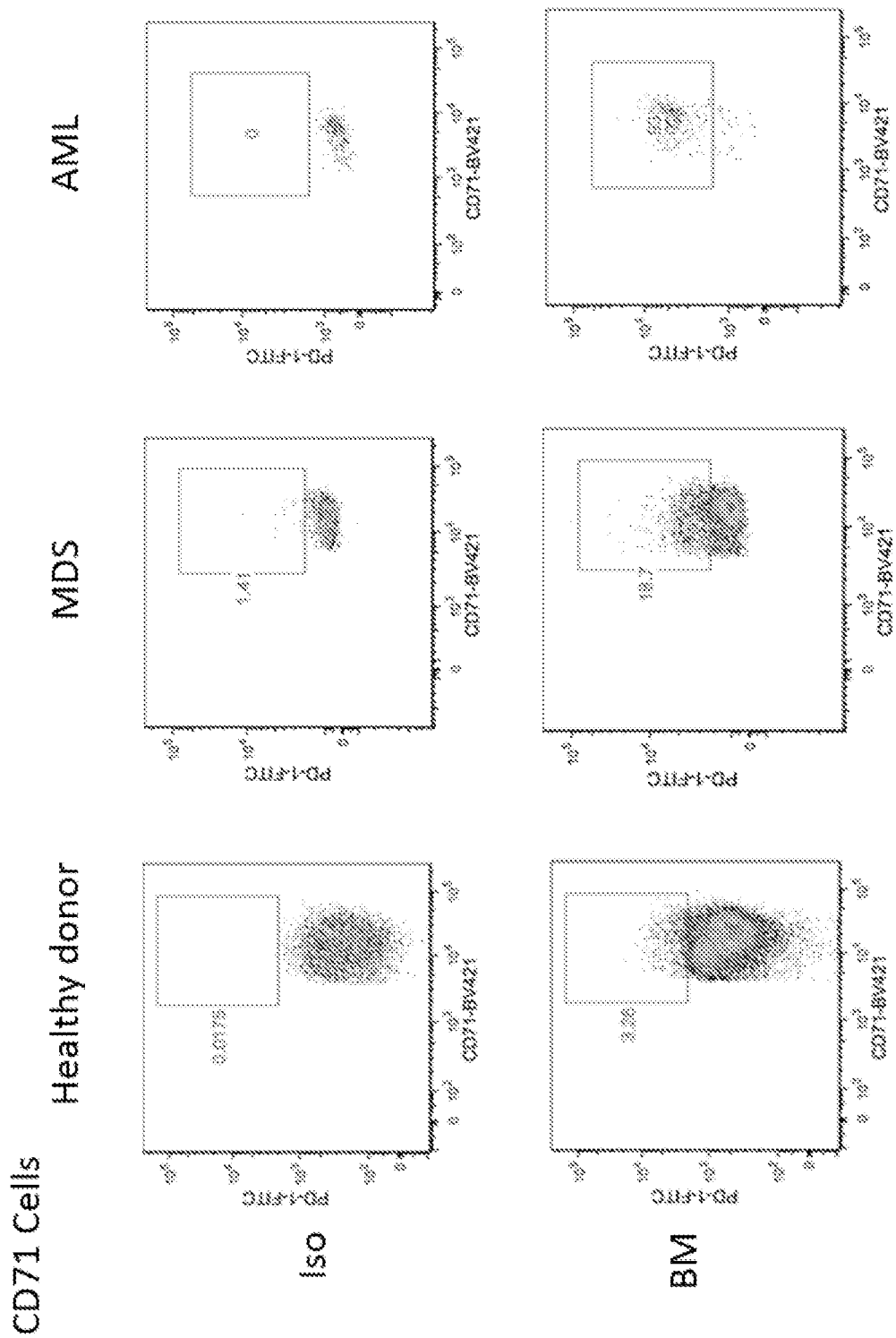
FIG. 15. PD1 expression in CD71 cells shifts during disease progression.
Figure 16:
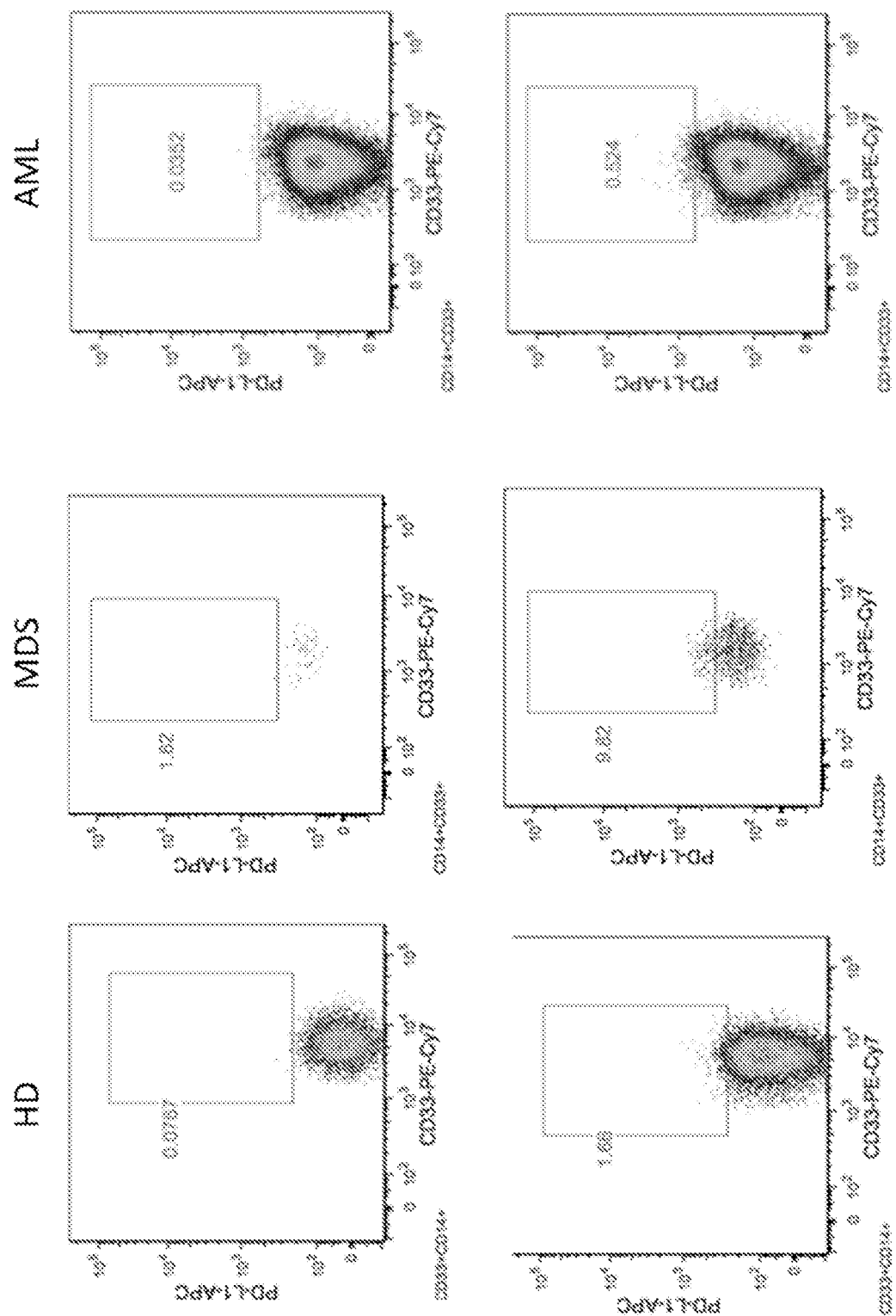
FIG. 16. PDL1 expression in CD33 cells shifts during disease progression.
Figure 17:
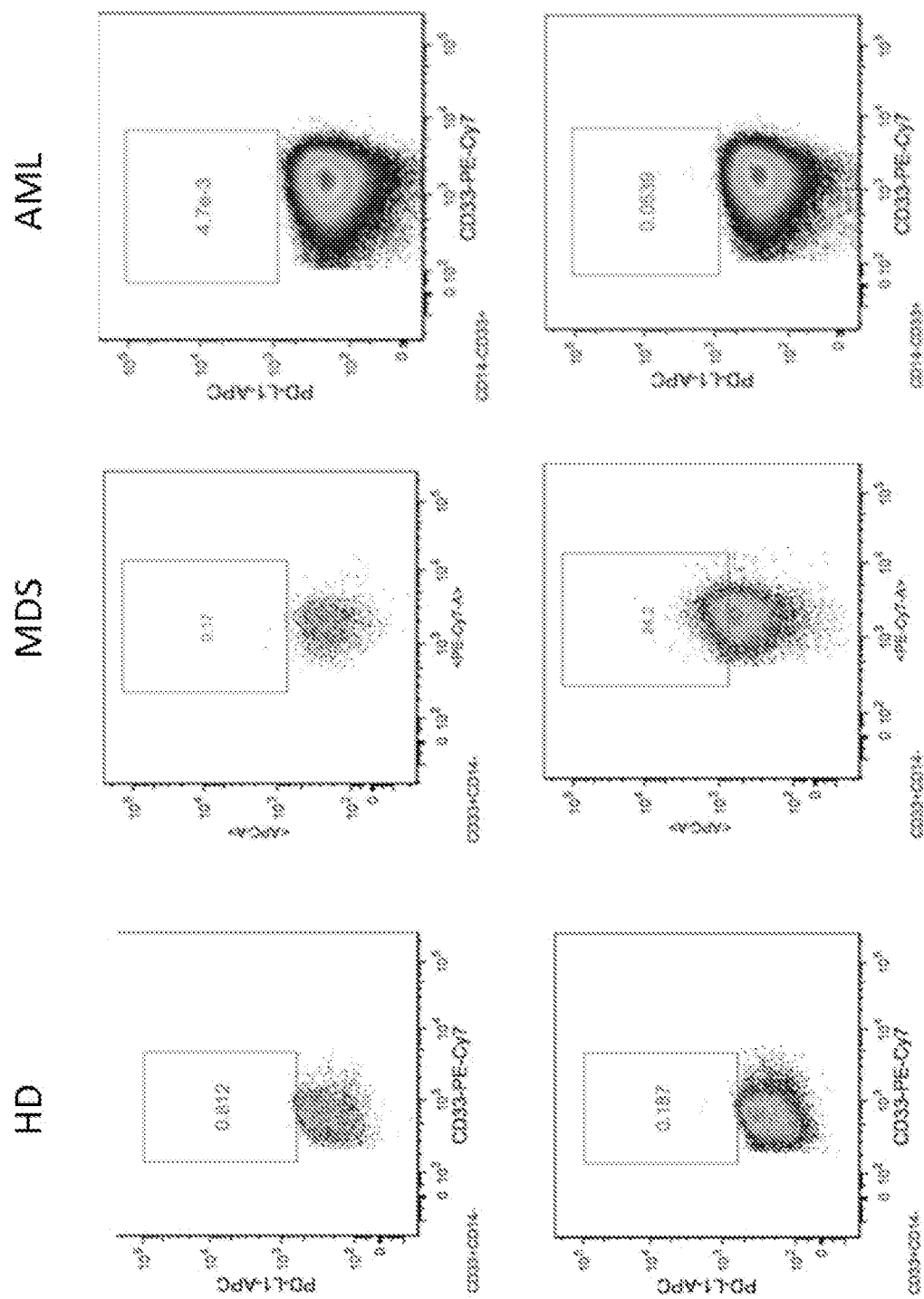
FIG. 17. PDL1 expression in MDSC shifts during disease progression.
Figure 18A:
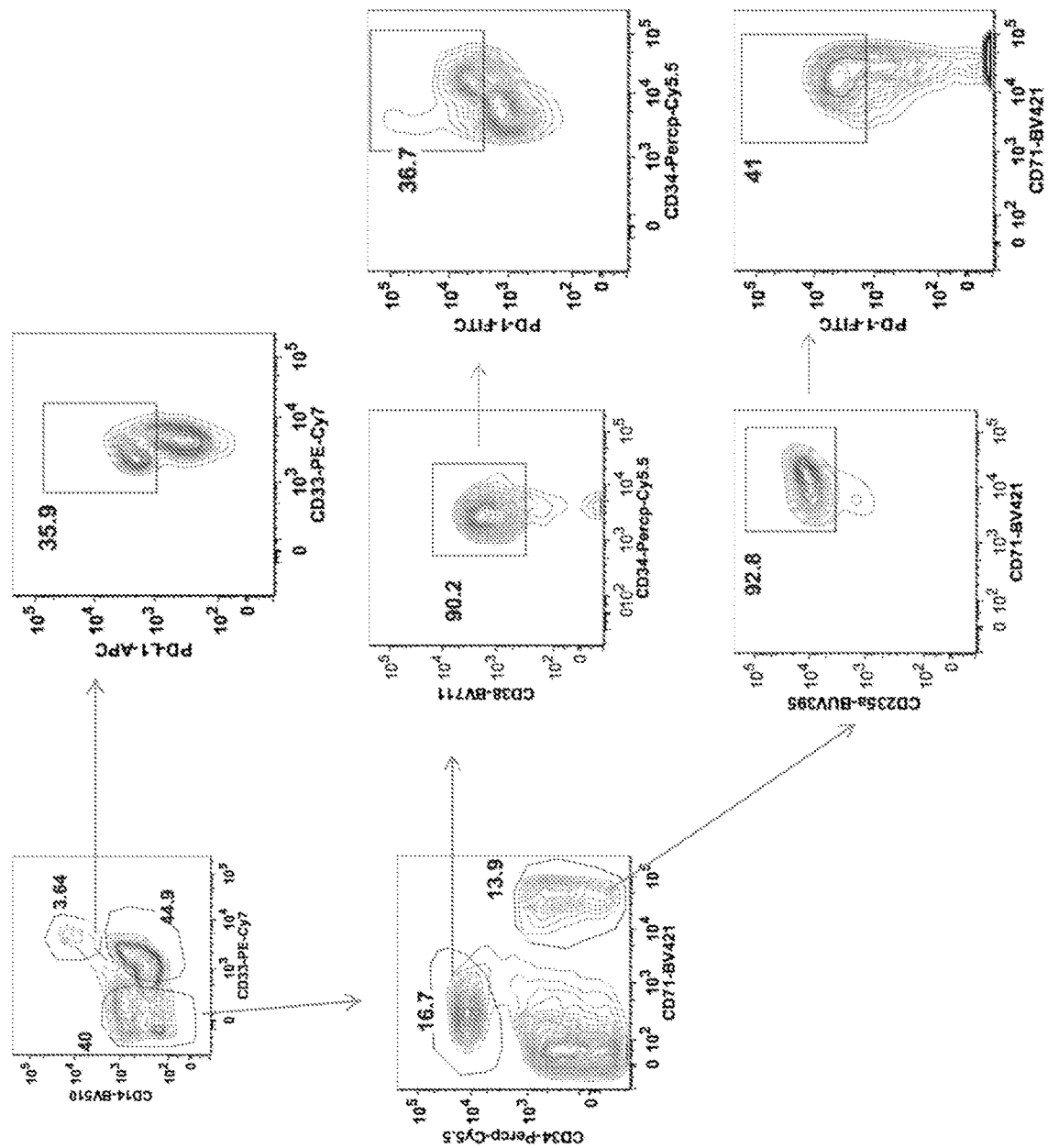
FIGS. 18A-18F. PD1 surface expression is increased in HSPC in MDS. (A) Fresh bone marrow cells from MDS patients or healthy donors were stained with antibodies: anti-CD33-PE-Cy7, anti-CD34-Percp-Cy5.5, anti-CD14-BV510, anti-CD71-BV421, anti-CD38-BV711, anti-CD235a-BUV395, anti-PD-1-FITC and anti-PD-L1-APC. Near infrared live/dead dye was used for distinction of live or dead cells. Flow acquisitions were performed using LSR II cytometer and analysis was done using live cells with flowjo. (B) PD-1 expression on erythroid precursors CD14−/CD33−/CD34−/CD71+/CD235a+ cells: cells positive for PD-1 surface expression were calculated based on FMO gate setting. (C) PD-1 expression on progenitors: Positive PD-1 surface expression on CD14−/CD33−/CD71−/CD34+/CD38+ progenitors was determined using FMO gates. (D) PD-L1 expression on CD14+/CD33+ cells. (E) PD-L1 expression on erythroid precursors CD14−/CD33−/CD34−/CD71+/CD235a+ cells. (F) PD-L1 expression on CD14−/CD33−/CD71−/CD34+/CD38+ progenitors. HD—healthy donor (n=6), MDS—myelodysplastic syndrome (n=10). Significance was determined using two-tailed unpaired t test with Welch's correction: *P<0.05, P<0.01, *P<0.001, error bars indicate mean±SEM.
Figure 18B:
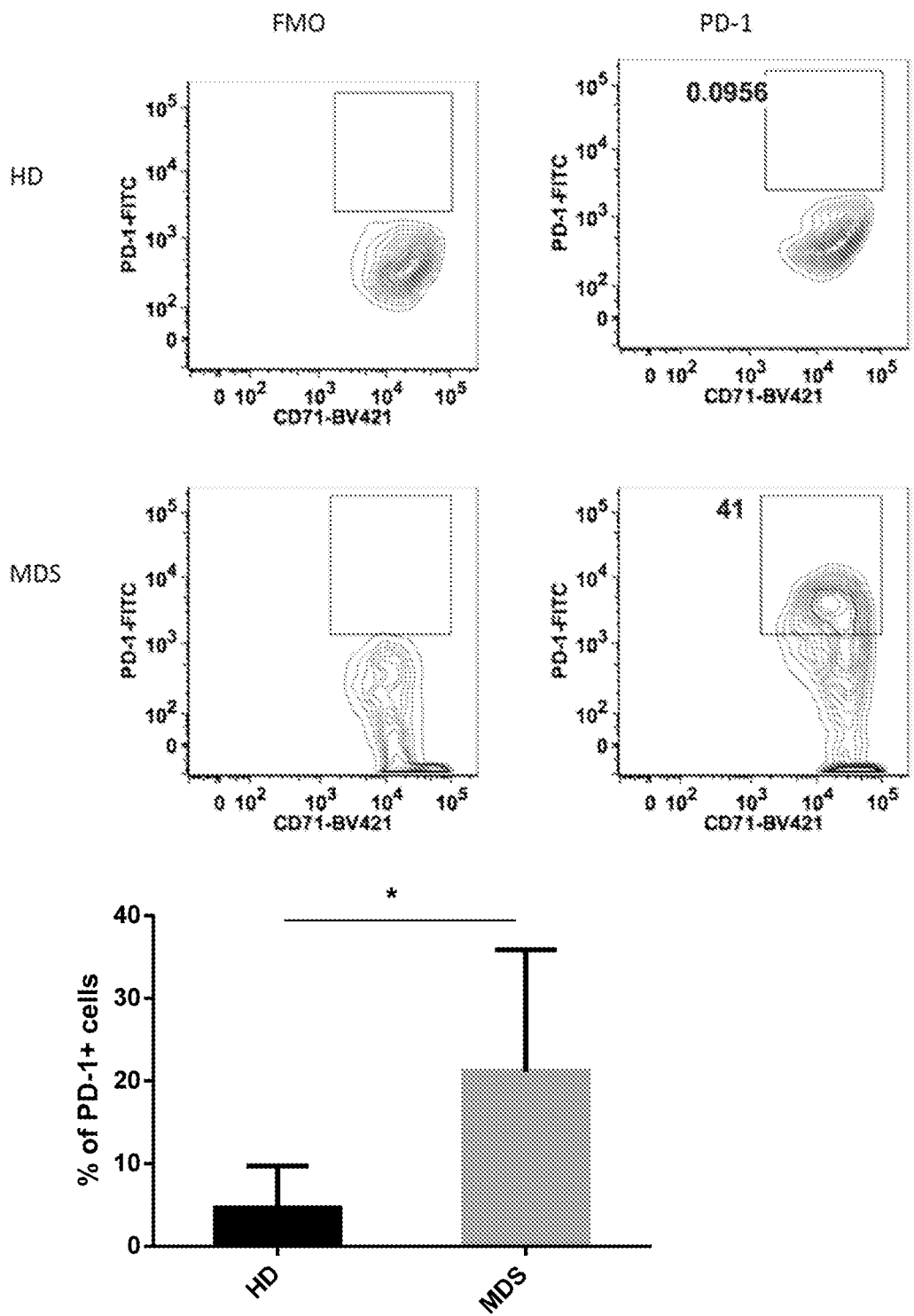
Figure 18C:
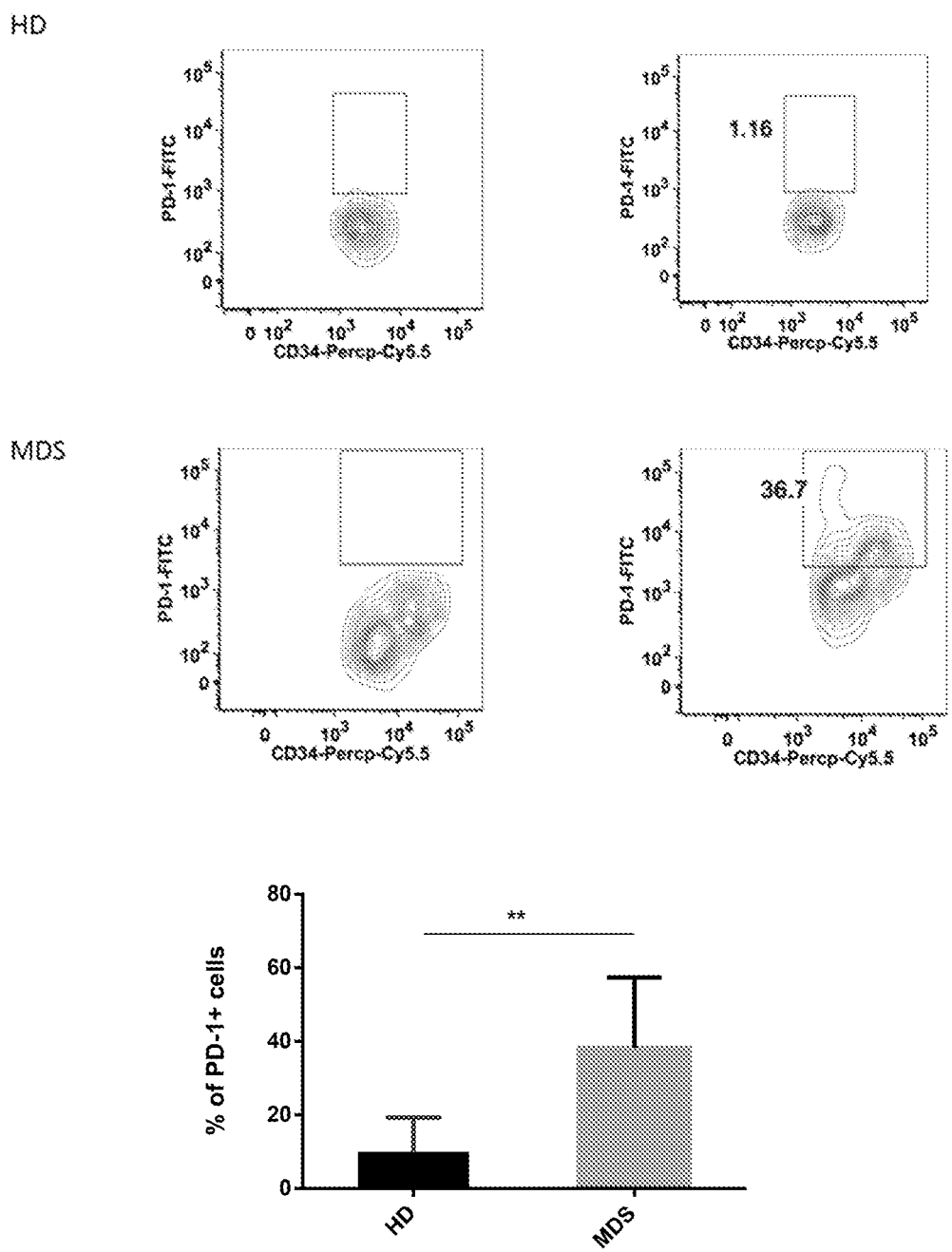
Figure 18D:
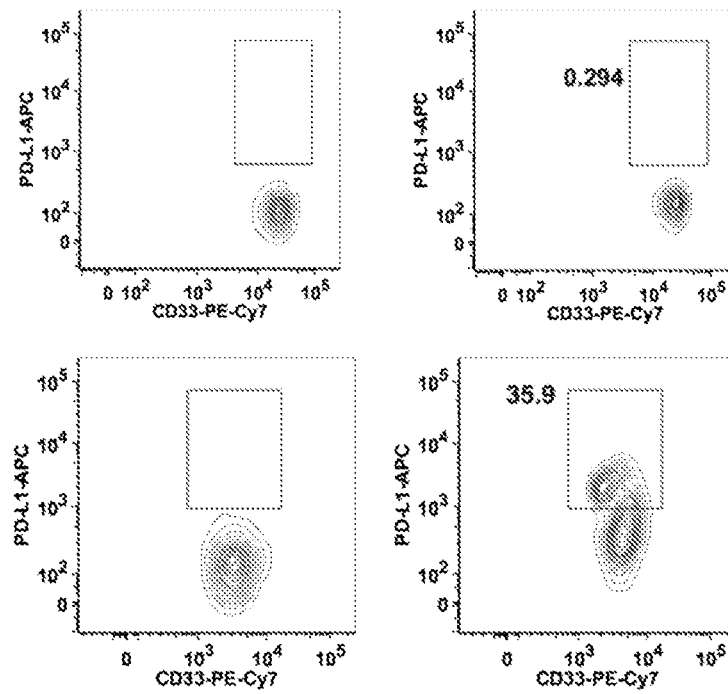
Figure 18D:
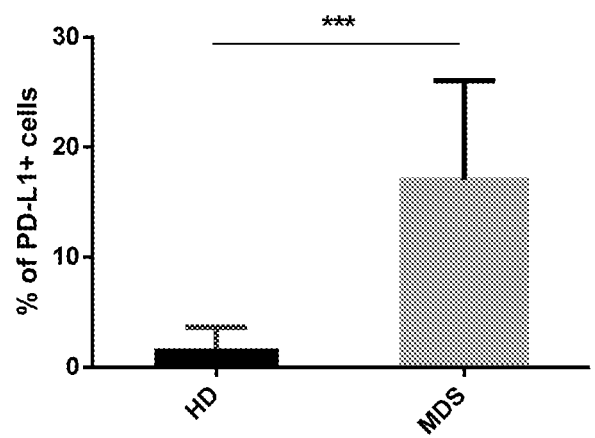
Figure 18E:
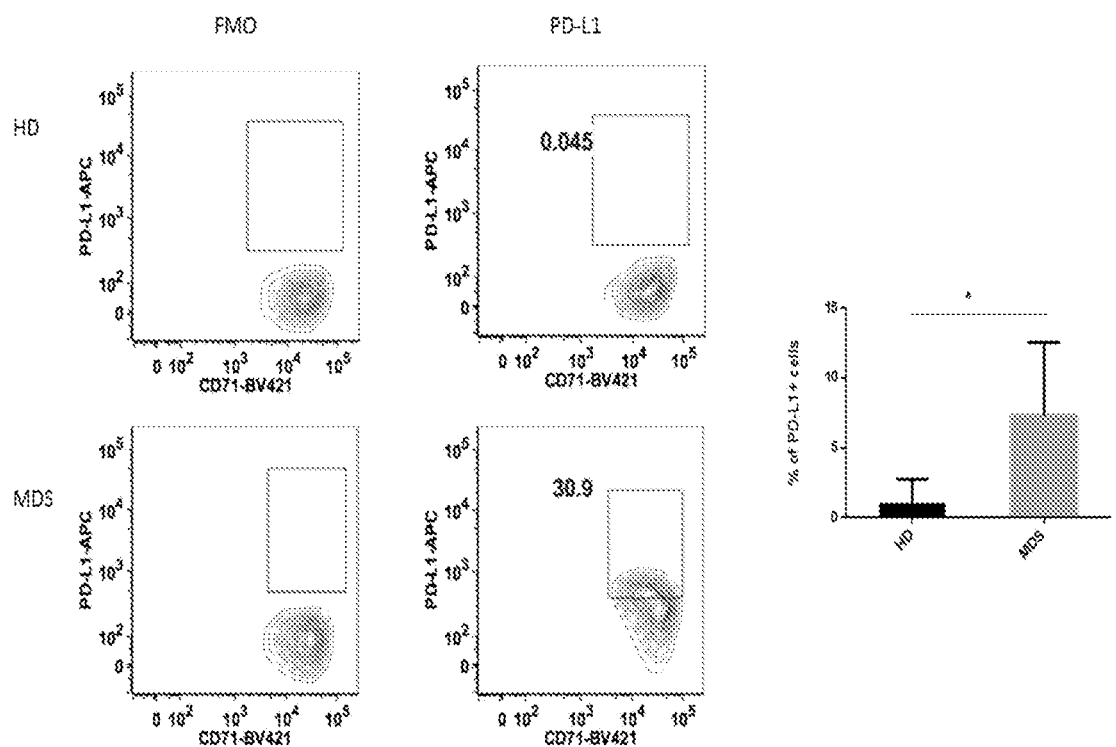
Figure 18F:
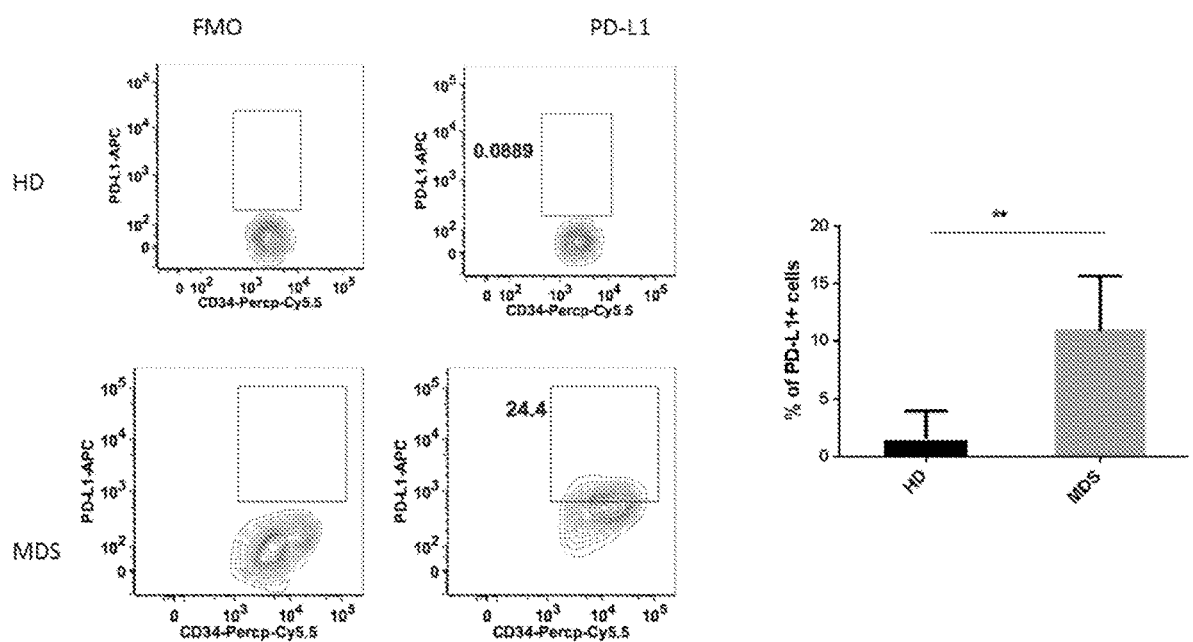
Figure 19A:
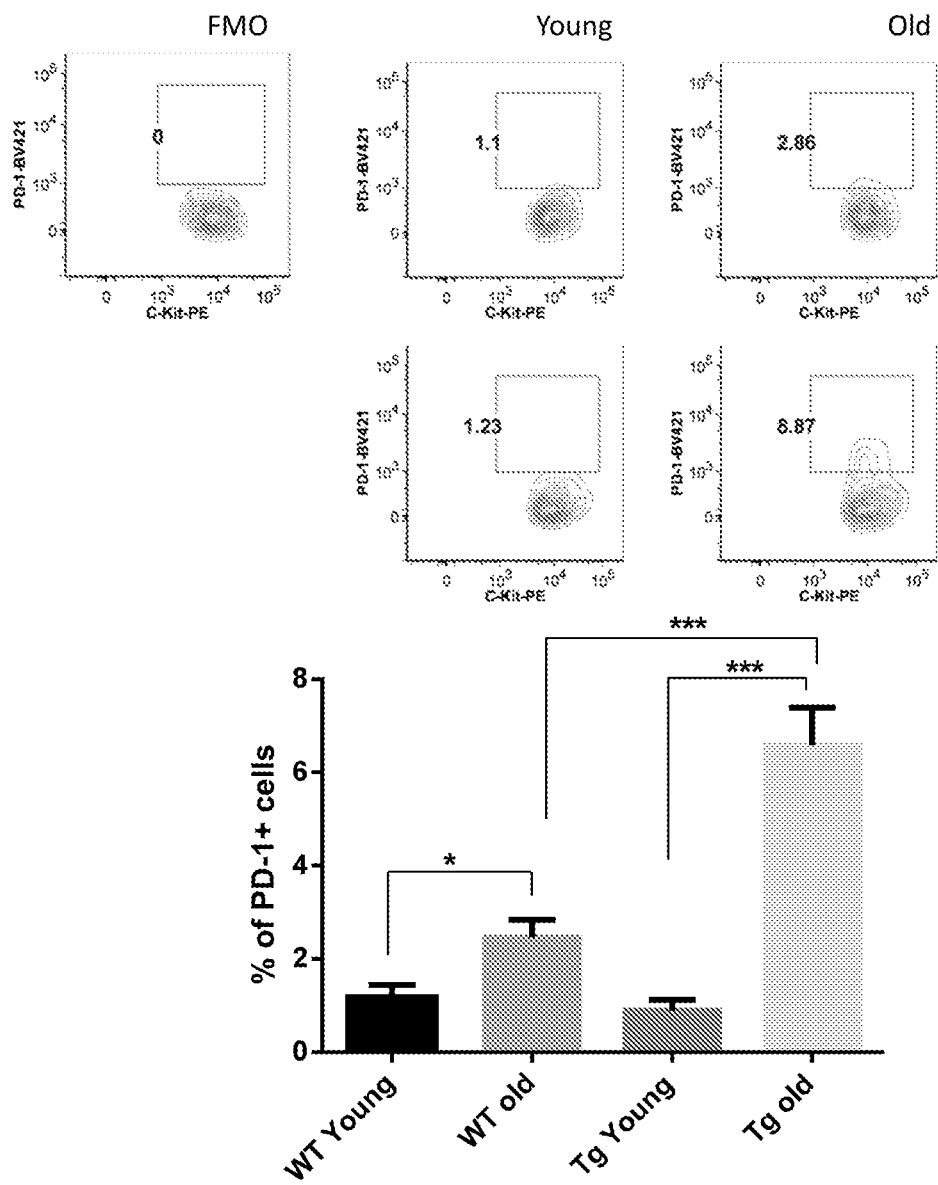
FIGS. 19A-19E. Overexpression of PD1 and PDL1 in aged S100A9Tg mice. FVB/n mice were sacrificed and bone marrow cells were stained with Abs: anti-c-Kit-Percp-Cy5.5, anti-Sca-1-PE, Lin-APC (including anti-CD3e, anti-CD11b, anti-CD45R/B220, anti-TER-119, anti-Gr-1), anti-PD-1-BV421, anti-PD-L1-BV711, anti-PD-L2-BUV395, and anti-CD16/32-PE-Cy7. Near infrared live/dead dye was used for distinction of live or dead cells. Flow acquisitions were performed using LSR II cytometer and analysis was done using live cells with flowjo. (A) PD-1 expression on Lin-common myeloid progenitor cells (CMP), Lin−/Sca-1−/c-Kit+/CD16/36+ cells, cells positive for PD-1 surface expression were calculated based on FMO gate setting. (B) and (C) PD-L1 expression on Lin-common myeloid progenitor cells (CMP). (D) and (E) PD-L1 expression on Gr-1+/CD11b-cells. Young mice age=3-month-old, old mice age=14-16 month-old; N=4 each group, experiment repeated three times. Significance was determined using two-tailed unpaired t test with Welch's correction: *P<0.05, P<0.01, *P<0.001, error bars indicate mean±SEM.
Figure 19B:
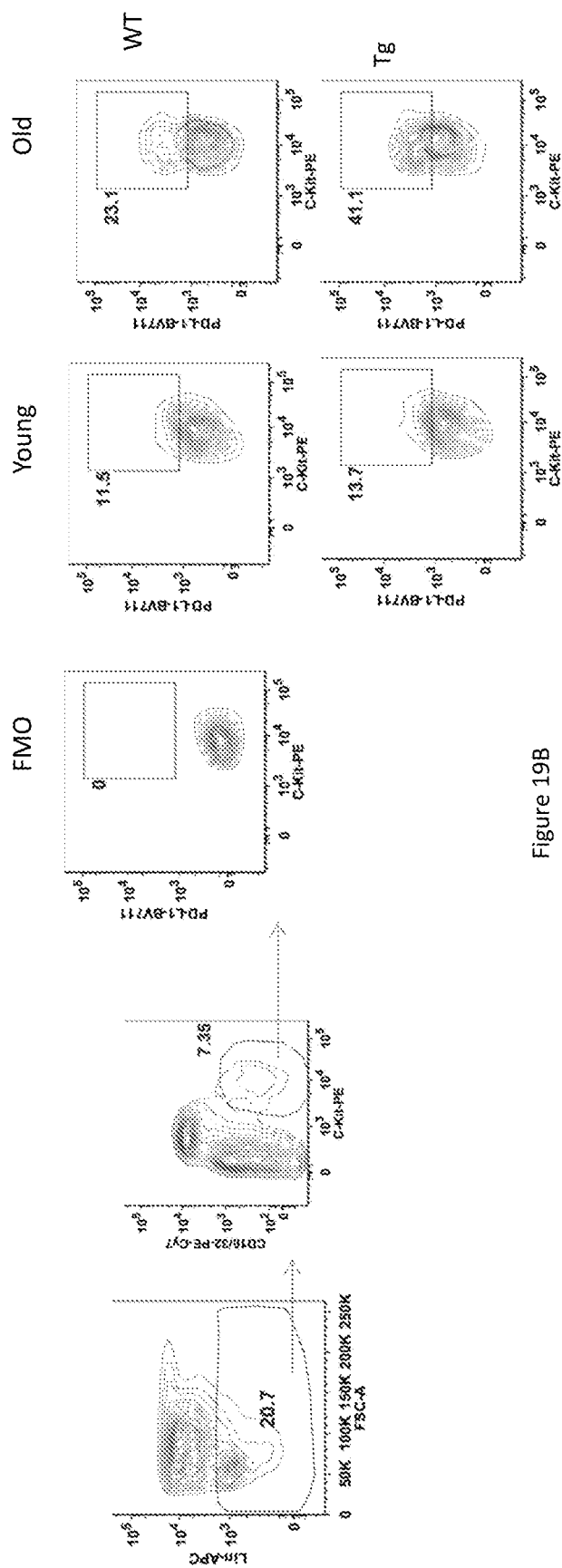
Figure 19C:
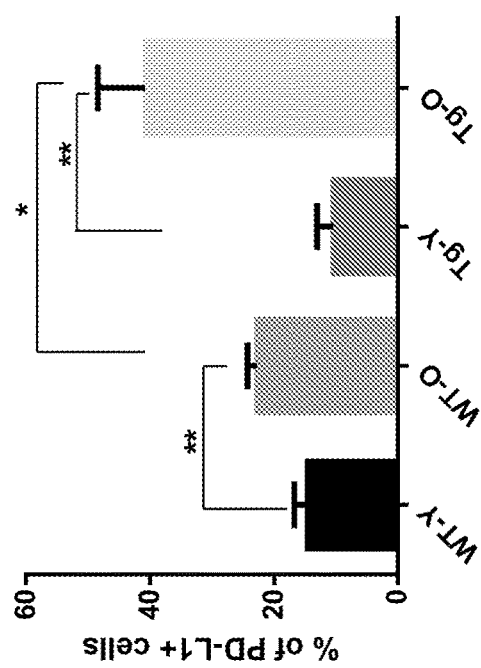
Figure 19D:
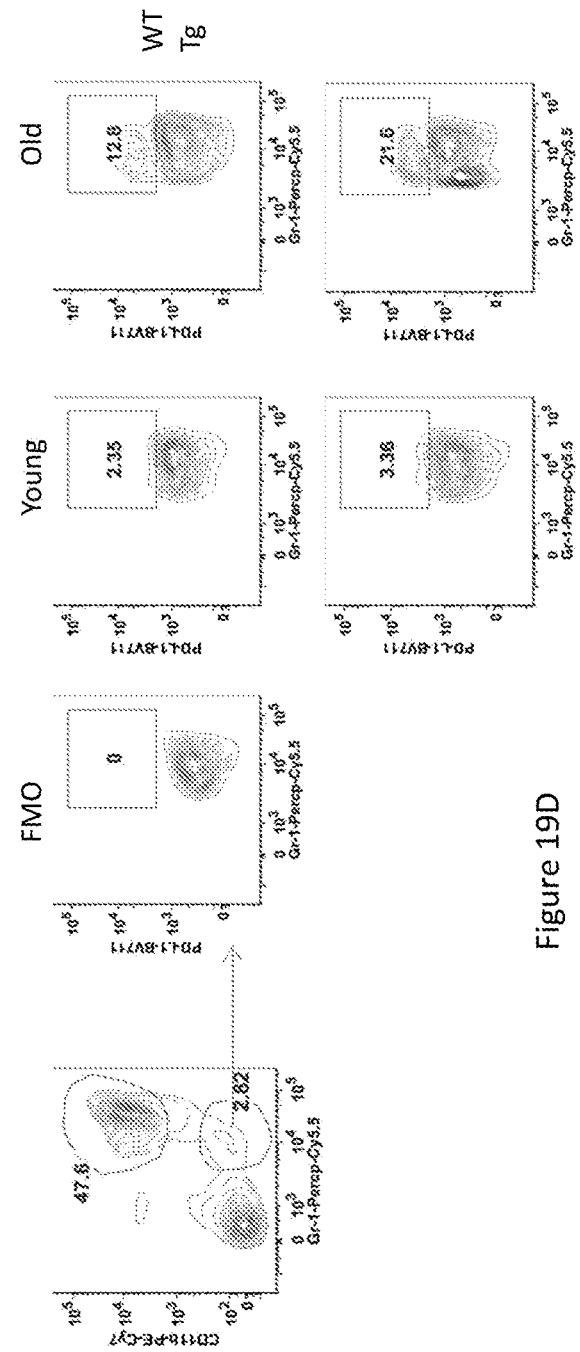
Figure 19E:
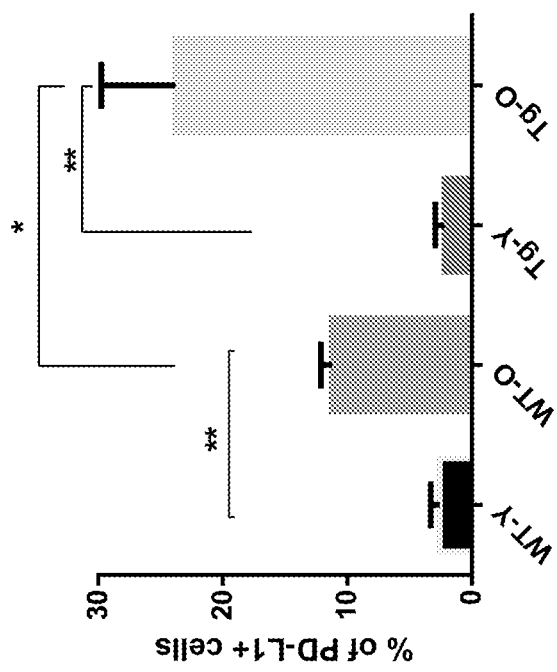
Figure 20A:
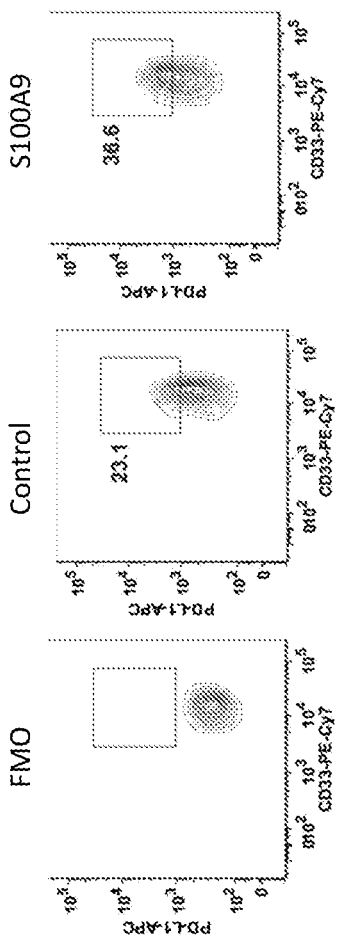
FIGS. 20A-20C. S100A9 directly induced the expression of PD-L1 on CD33+ cells and PD-1 expression on CD34 and CD71 cells. One and half million of BM cells from Healthy donor were placed per well in 24-well plate, cultured with IgG or S100A9. After 48 h, cells were collected and stained with antibodies: anti-CD33-PE-Cy7, anti-CD34-Percp-Cy5.5, anti-CD14-BV510, anti-CD71-BV421, anti-CD38-BV711, anti-CD235a-BUV395, anti-PD-1-FITC and anti-PD-L1-APC. Near infrared live/dead dye was used for distinction of live or dead cells. Flow acquisitions were performed using LSR II cytometer and analysis was done using live cells with flowjo. (A) PD-L1 expression on CD14+/CD33+: cells positive for PD-L1 surface expression were calculated based on FMO gate setting. (B) and (C) PD-1 expression on progenitors by S100A9 or PT plasma, respectively. Positive PD-1 surface expression on CD14−/CD33−/CD71−/CD34+/CD38+ progenitors was determined using FMO gates. HD—healthy donor (n=6), MDS—myelodysplastic syndrome (n=10). Significance was determined using two-tailed unpaired t test with Welch's correction: *P<0.05, P<0.01, *P<0.001, error bars indicate mean±SEM.
Figure 20A:
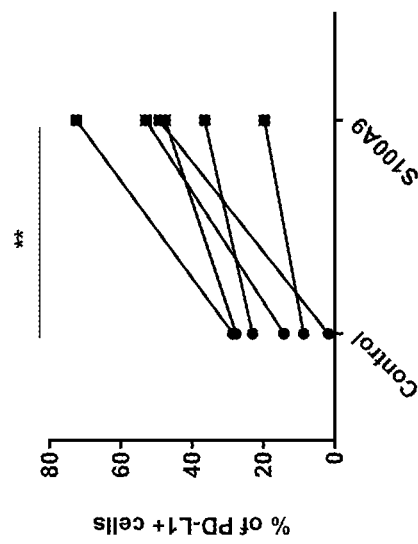
Figure 20B:
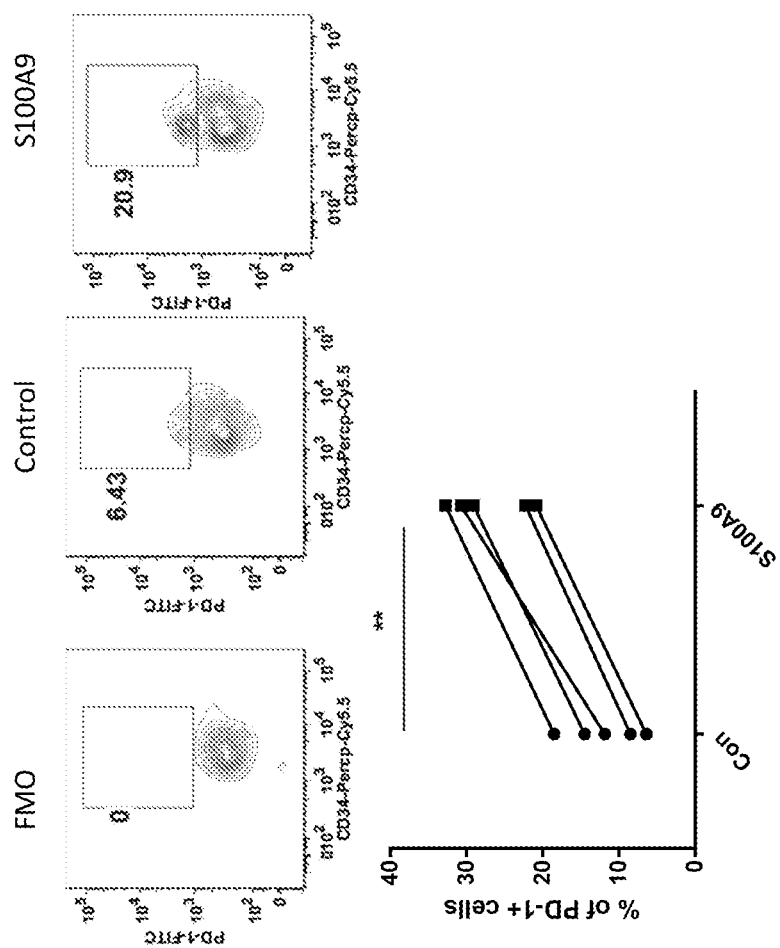
Figure 20C:
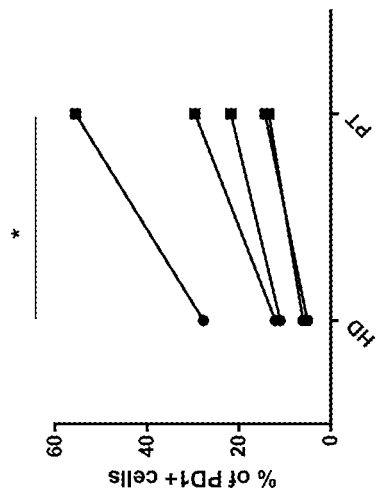
Figure 20C:
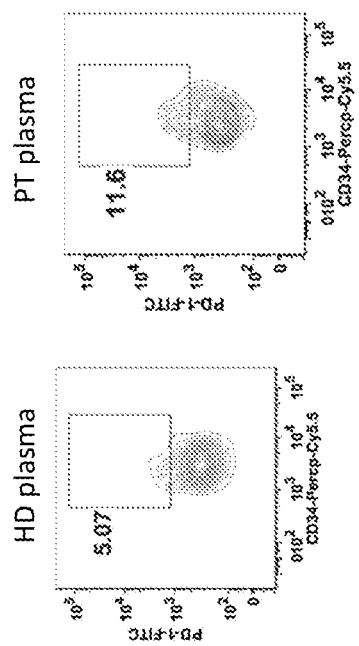

As shown in FIGS. 14 and 15, PD1 expression is greatly increased in MDS and continues to rise during progression to AML. PDL1 is only increased in MDS in CD33 cells and MDSC but not in AML. (FIGS. 16 and 17).

As shown in FIG. 18, PD1 surface expression is increased in HSPC in MDS.

As shown in FIG. 19, the overexpression of PD1 and PDL1 was performed in aged S100A9Tg mice.

As shown in FIG. 20, S100A9 directly induced the expression of PD-L1 on CD33+ cells and PD-1 expression on CD34 and CD71 cells.

Figure 21:
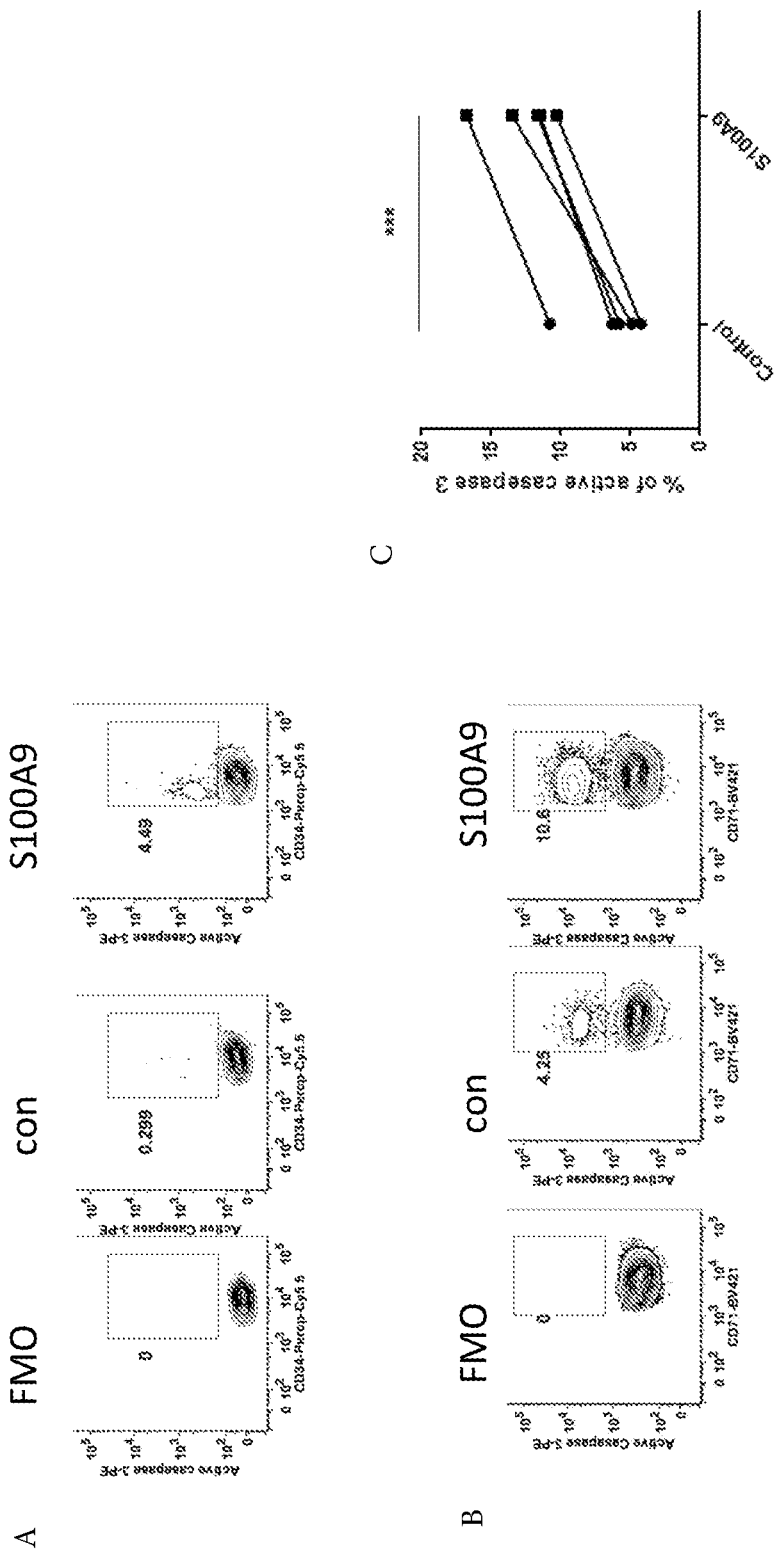
FIG. 21. Increased the expression of PD-1 and PD-L1 induced cell death. One and half million of BM cells from Healthy donor were placed per well in 24-well plate, cultured with IgG or S100A9. After 48 h, cells were collected and stained for cell surface with antibodies: anti-CD33-PE-Cy7, anti-CD34-Percp-Cy5.5, anti-CD14-BV510, anti- CD71-BV421, anti-CD38-BV711, and anti-CD235a-BUV395, then cells were fixed/permeabilized and stained with anti-active caspase 3-PE according to manufacturer's protocol (BD Biosciences). Near infrared live/dead dye was used for distinction of live or dead cells. Flow acquisitions were performed using LSR II cytometer and analysis was done using live cells with flowjo. (A) PD-L1 expression on CD14+/CD33+: cells positive for PD-L1 surface expression were calculated based on FMO gate setting. (B) and (C). PD-1 expression on progenitors by S100A9 or PT plasma, respectively: Positive PD-1 surface expression on CD14−/CD33−/CD71−/CD34+/CD38+ progenitors was determined using FMO gates. HD—healthy donor (n=6), MDS—myelodysplastic syndrome (n=10). Significance was determined using two-tailed unpaired t test with Welch's correction: *$P<0.05$, $P<0.01$, *$P<0.001$, error bars indicate mean±SEM.

As shown in FIG. 21, increased expression of PD-1 and PD-L1 induced cell death.

Figure 22:
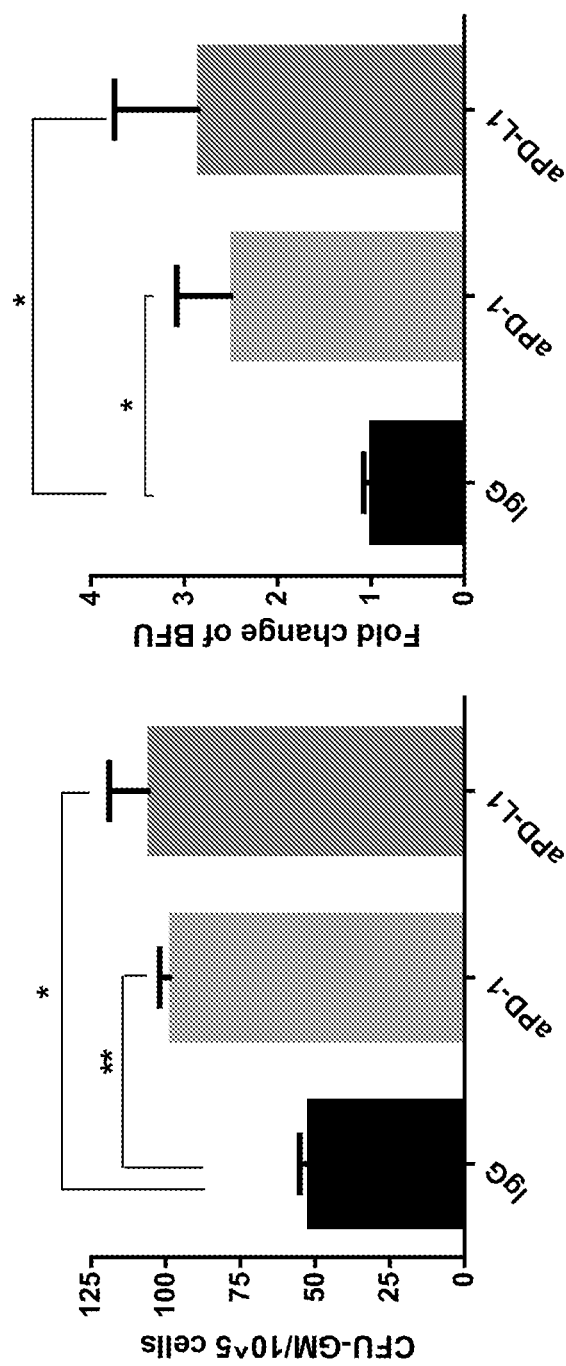
FIG. 22. Colony formation by anti-PD-1 and anti-PD-L1: patient BM cells were treated with IgG, aPD-1 or aPD-L1 for 48 h. Then colony formation assay was performed using $10^5$ wells.

As shown in FIG. 22, colony formation was increased by anti-PD-1 and anti-PD-L1 treatment of patient BM cells.

Figure 23:
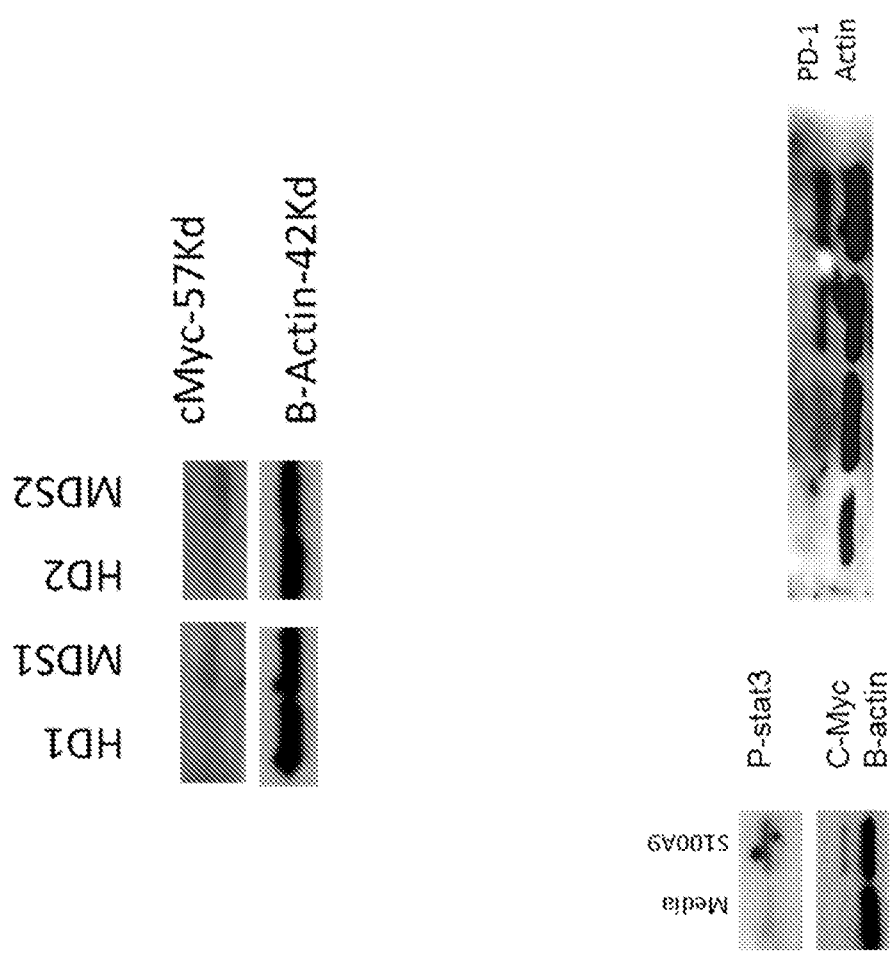
FIG. 23. C-Myc increased in MDS, and S100A9 induced C-Myc expression. HD BM cultured (left panel) with S100A9 for 48 h, induced p-stat3 and cMyc. Right panel, HD BM cells 48 h treatment.

As shown in FIG. 23, C-Myc was increased in MDS, and S100A9 induced C-Myc expression.

The American Cancer Society predicts nearly 20,000 patients will develop AML in 2016 with a 5-year survival for the average patient of 5-10%. The standard method of assessing patient mortality risk is the International Prognostic Scoring System (IPSS) which assigns patients to one of several risk categories. Although certain risk categories are associated with increased likelihood of progressing to AML, the IPSS underestimates the risk of major symptoms by up to 20%. Genetic data are thought to better inform the risk of MDS patients progressing to AML.

The expression of PD-1 is shown to be elevated five-fold in MDS patients and elevated up to 5-fold further in AML patients, while that of PD-L1 decreases nearly 450-fold between MDS and AML patients. Ongoing clinical trials have shown anti-PD-1 therapeutics caused a remarkable decline in peripheral blood blasts in a single case of AML, a reversal of the hallmark criterion for disease progression.

The market for genetic MDS categorization is evidenced by the MDS Molecular Profile available from Genoptix®, a gene sequencing test that provides genetic mutation data that can be integrated into the IPSS to better assess prognostic risk. Mutations in one of the tested genes, RUNX1, are prognostic for rapid progression to AML.

As shown herein, the methods provide a risk stratification tool that measures the expression of PD-1 on $CD71^+$ and $CD34^+$ progenitor cells or the expression of PD-L1 on $CD33^+$ myeloid-derived suppressor cells, utilizing an increase in PD-1 or a decrease in PD-L1 levels to indicate risk of progression from MDS to AML. This method is based on data illustrating that PD-1 levels are elevated nearly 5-fold in $CD71^+$ $PD-1^+$ progenitor cells from AML compared to MDS patients, while PD-L1 decreases nearly 450-fold in $CD33^-$ $CD14^+$ myeloid-derived suppressor cells in AML compared to MDS patients.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A method for treating acute myelogenous leukemia (AML) in a subject, comprising:
    assaying a sample from the subject for the expression of PD-1 on CD71+ and CD34+ progenitor cells, the expression of PD-L1 on CD33+ myeloid derived stem cells (MDSCs), or a combination thereof,
    detecting an increase in PD-1 expression on progenitor cells or decrease in PD-L1 expression on MDSCs as an indication of progression from myelodysplastic syndrome (MDS) to AML, and
    treating the subject for AML,
    wherein the increase in PD-1 expression on progenitor cells is at least 5 fold relative to a healthy control,
    and wherein the decrease in PD-L1 expression on MDSCs is at least 450 fold relative to a healthy control.

2. The method of claim 1, comprising assaying a sample from the subject for the expression of PD-1 on CD71+ and CD34+ progenitor cells, wherein an increase in PD-1 expression on progenitor cells is an indication of progression from MDS to AML.

3. The method of claim 1, comprising assaying a sample from the subject for the expression of PD-L1 on CD33+ myeloid derived stem cells (MDSCs), wherein a decrease in PD-L1 expression on MDSCs is an indication of progression from MDS to AML.

4. The method of claim 1, comprising assaying a sample from the subject for the expression of PD-1 on CD71+ and CD34+ progenitor cells and the expression of PD-L1 on CD33+ myeloid derived stem cells (MDSCs), wherein an increase in PD-1 expression on progenitor cells and a decrease in PD-L1 expression on MDSCs is an indication of progression from MDS to AML.

5. The method of claim 1, wherein the treating the subject for AML comprises administration of a chemotherapeutic agent.

6. The method of claim 5, wherein the chemotherapeutic agent is selected from cytarabine, daunorubicin, idarubicin, mitoxantrone, vincristine, cladribine, fludarabine, topotecan, etoposide, 6-thioguanine, hydroxyurea, corticosteroid drugs, methotrexate, 6-mercaptopurine, azacitidine, and decitabine.

7. The method of claim 1, wherein the treating the subject for AML comprises administration of an immunotherapeutic agent.

8. The method of claim 7, wherein the immunotherapeutic agent is selected from an anti-PD1 antibody, an anti-PDL1 antibody, an anti-CTLA4 antibody, and a combination thereof.

9. The method of claim 1, wherein the sample is a blood sample.

* * * * *